(12) United States Patent
Weber

(10) Patent No.: US 9,078,777 B2
(45) Date of Patent: Jul. 14, 2015

(54) STENT WITH NON-ROUND CROSS-SECTION IN AN UNEXPANDED STATE

(75) Inventor: Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1915 days.

(21) Appl. No.: 12/170,222

(22) Filed: Jul. 9, 2008

(65) Prior Publication Data

US 2010/0010620 A1    Jan. 14, 2010

(51) Int. Cl.
| | |
|---|---|
| A61F 2/06 | (2013.01) |
| *A61F 2/915* | (2013.01) |
| *A61F 2/91* | (2013.01) |
| A61F 2/90 | (2013.01) |
| A61F 2/844 | (2013.01) |
| A61F 2/95 | (2013.01) |

(52) U.S. Cl.
CPC . *A61F 2/915* (2013.01); *A61F 2/91* (2013.01); A61F 2/844 (2013.01); A61F 2/90 (2013.01); A61F 2/95 (2013.01); A61F 2002/9155 (2013.01); A61F 2002/91508 (2013.01); A61F 2002/91516 (2013.01); A61F 2002/91558 (2013.01); A61F 2002/91575 (2013.01); A61F 2002/91583 (2013.01); A61F 2210/0004 (2013.01); A61F 2210/0014 (2013.01); A61F 2230/001 (2013.01); A61F 2230/0002 (2013.01); A61F 2230/0006 (2013.01); A61F 2230/0008 (2013.01); A61F 2230/0013 (2013.01); A61F 2230/0015 (2013.01); A61F 2230/0034 (2013.01); A61F 2230/0045 (2013.01); A61F 2230/0069 (2013.01); A61F 2250/001 (2013.01); A61F 2250/0039 (2013.01); A61F 2250/0048 (2013.01); A61F 2250/0067 (2013.01); A61F 2250/0098 (2013.01); A61F 2310/00017 (2013.01); A61F 2310/00041 (2013.01); A61F 2310/00083 (2013.01); A61F 2310/00389 (2013.01)

(58) Field of Classification Search
CPC .................................... A61F 2/82; A61F 2/844
USPC .......................................................... 623/1.15
See application file for complete search history.

(56) References Cited

U.S. PATENT DOCUMENTS

| | | | |
|---|---|---|---|
| 5,873,906 A * | 2/1999 | Lau et al. | 128/898 |
| 6,017,362 A | 1/2000 | Lau | |
| 6,241,762 B1 * | 6/2001 | Shanley | 623/1.17 |
| 6,287,332 B1 | 9/2001 | Bolz et al. | |
| 2002/0144757 A1 | 10/2002 | Craig et al. | |

(Continued)

OTHER PUBLICATIONS

Merriam-Webster definiion of "state", accessed online Jan. 24, 2012.*

(Continued)

*Primary Examiner* — Jacqueline Woznicki
(74) *Attorney, Agent, or Firm* — Vidas, Arrett & Steinkraus, P.A.

(57) ABSTRACT

A stent has a circumference and a plurality of members that define a lumen. The stent has three stable states, which include an unexpanded state, a partially deployed state, and a deployed state. The lumen has a first cross-sectional shape in the unexpanded state, a second cross-sectional shape in the partially deployed state and a third cross-sectional shape in the deployed state. The first cross-sectional shape of the lumen is different from the second and third cross-sectional shapes of the lumen, and the first cross-sectional shape of the lumen is a non-round shaped cross-sectional shape.

20 Claims, 18 Drawing Sheets

(56) References Cited

U.S. PATENT DOCUMENTS

| | | |
|---|---|---|
| 2003/0018380 A1 | 1/2003 | Craig et al. |
| 2003/0077200 A1 | 4/2003 | Craig et al. |
| 2004/0143317 A1 | 7/2004 | Stinson et al. |
| 2005/0070990 A1 | 3/2005 | Stinson |
| 2006/0153729 A1 | 7/2006 | Stinson et al. |
| 2007/0123970 A1 | 5/2007 | Lenz |
| 2007/0135904 A1 | 6/2007 | Eidenschink et al. |
| 2007/0156231 A1 | 7/2007 | Weber |
| 2007/0156248 A1 | 7/2007 | Marco et al. |
| 2007/0270940 A1 | 11/2007 | Doty |
| 2007/0282432 A1 | 12/2007 | Stinson et al. |
| 2007/0288084 A1 | 12/2007 | Lee et al. |
| 2007/0288085 A1 | 12/2007 | Furst |
| 2008/0071355 A1 | 3/2008 | Weber et al. |

OTHER PUBLICATIONS

Merriam-Webster definiion of "very", accessed online Jan. 24, 2012.*
Merriam-Webster definiion of "circumferential", accessed online Jan. 24, 2012.*
Merriam-Webster definiion of "ring", accessed online Jan. 24, 2012.*

* cited by examiner

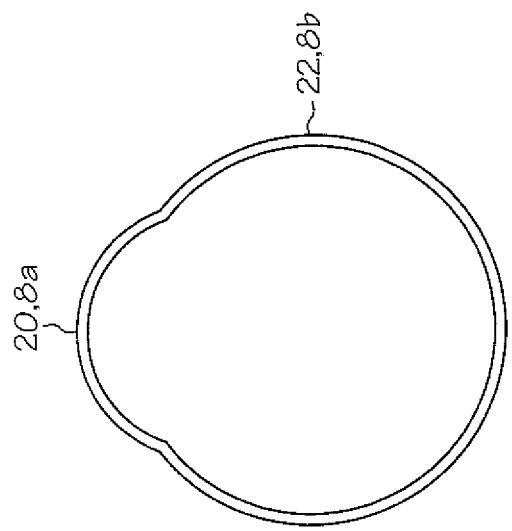
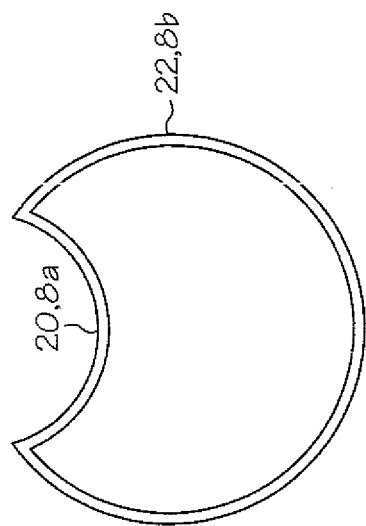

STENT WITH NON-ROUND CROSS-SECTION IN AN UNEXPANDED STATE

CROSS-REFERENCE TO RELATED APPLICATIONS

Not Applicable

STATEMENT REGARDING FEDERALLY SPONSORED RESEARCH

Not Applicable

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced shape, optionally restrained in a radially compressed shape by a sheath and/or catheter, is delivered by a stent delivery system or "introducer" to the site where it is required The introducer may enter the body from an access location outside the body, such as through the patient's skin, or by a "cut down" technique in which the entry blood vessel is exposed by minor surgical means Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable)

Stents may be created by methods including cutting or etching a design from a tubular stock, from a flat sheet which is cut or etched and which is subsequently rolled or from one or more interwoven wires or braids Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §156(a) exists All US patents and applications and all other published documents mentioned anywhere in this application are incorporated herein by reference in their entirety Without limiting the scope of the invention a brief summary of some of the claimed embodiments of the invention is set forth below Additional details of the summarized embodiments of the invention and/or additional embodiments of the invention may be found in the Detailed Description of the Invention below

BRIEF SUMMARY OF THE INVENTION

In at least one embodiment, the invention is directed to a stent comprising a first section and a second section and having three states, an unexpanded state, a partially deployed state and a deployed state. In some embodiments, the second section has a first shape in each of the states. In other embodiments, the first section has a first shape in the unexpanded state and a second shape in both the partially deployed state and the deployed state In some embodiments, the stent defines a lumen that has a first cross-sectional shape in the unexpanded state and a second cross-sectional shape in both the partially deployed state and the deployed state, where the first cross-sectional shape is different from the second cross-sectional shape. In one embodiment the first cross-sectional shape is a non-round shaped cross-sectional shape and the second cross-sectional shape is a round-shaped cross-sectional shape. It is within the scope of the invention for the stent to be made from any material or combination of materials These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention

BRIEF DESCRIPTION OF THE SEVERAL VIEWS OF THE DRAWING(S)

A detailed description of the invention is hereafter described with specific reference being made to the drawings.

FIG. 20a is a cross-section of a stent embodiment formed from two tubes FIG. 20b is a cross-section of another stent embodiment formed from two tubes.

DETAILED DESCRIPTION OF THE INVENTION

Figure 1:
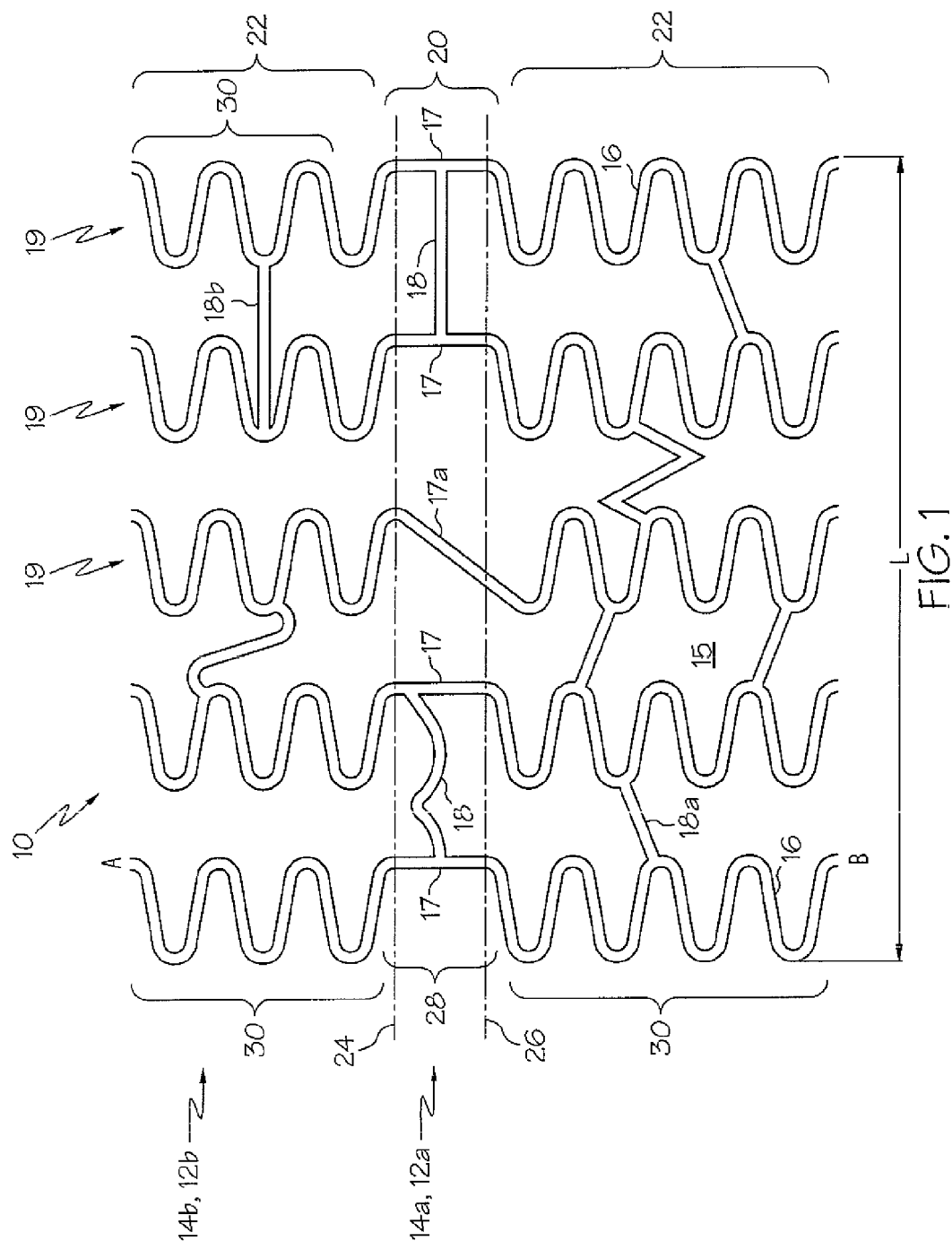
FIG. 1 is a flat view of a stent pattern that two sections forming the circumference of the stent.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Figure 8:
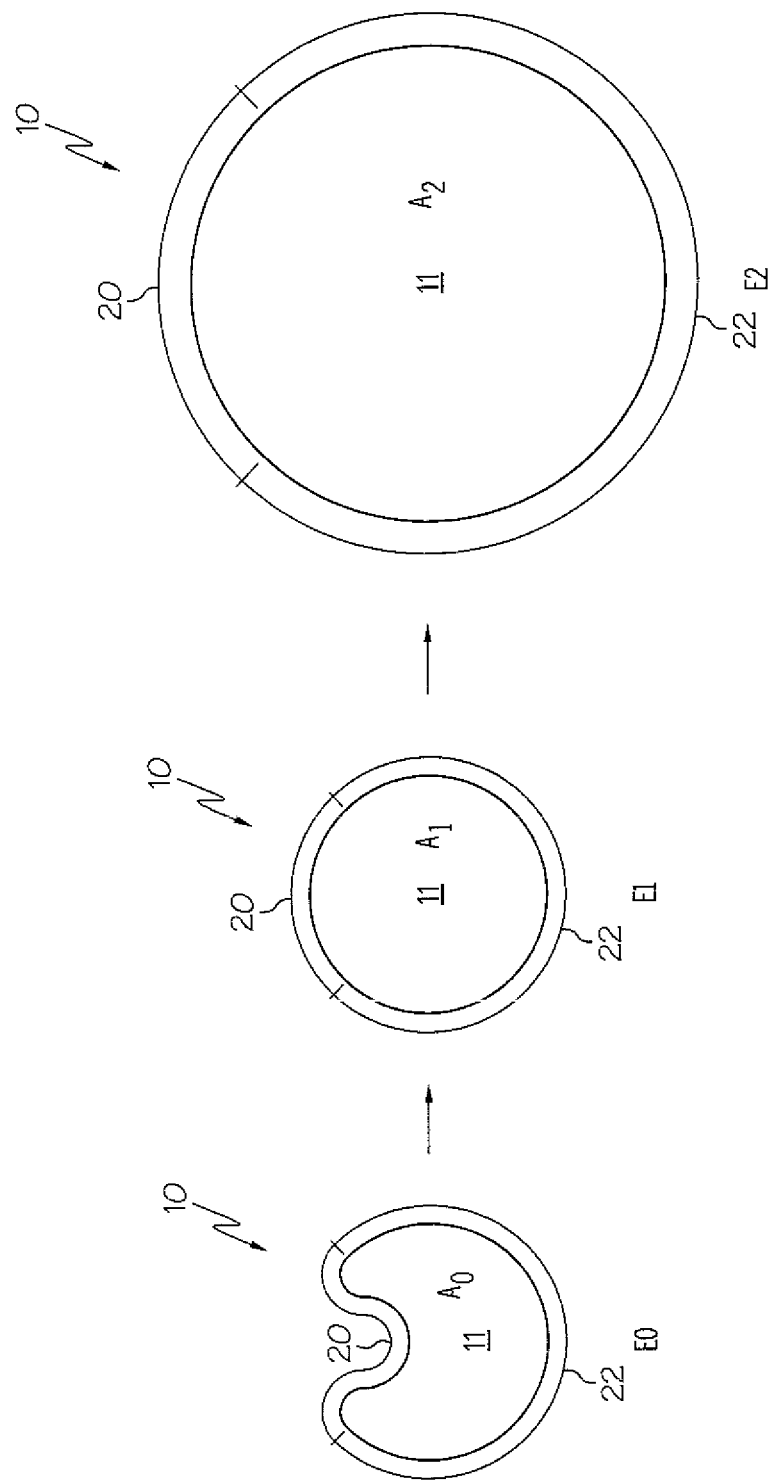
FIG. 8 shows the stent of FIG. 7 expanding from the first state, the unexpanded state to the second state, the partially deployed state, and then to the third state, the deployed state.
Figure 11:
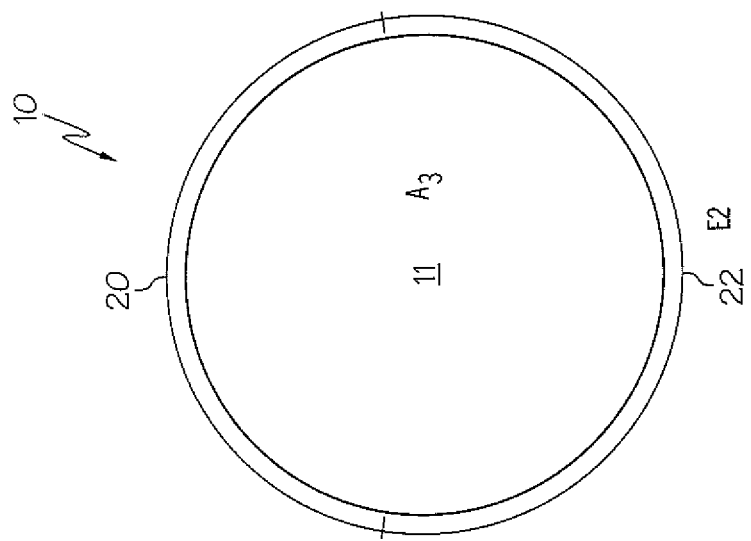
FIG. 11 is the stent of FIG. 9 is the third state, the deployed state.

In at least one embodiment, the invention is directed toward a stent 10 which is constructed and arranged so that the stent 10 has at least three stable states (E0, E1, E2), an unexpanded state (E0), a partially deployed state (E1) and a deployed state (E2), as shown in FIG. 8. As used in this application, the unexpanded state (E0) refers to a stent 10 that is ready to be crimped onto a balloon catheter 50 and a stent 10 that is not ready to be crimped onto a balloon catheter 50 is in a pre-unexpanded state (pre-E0), as discussed in greater detail below. In some embodiments, the stent 10 has only three states, the unexpanded state (E0), the partially deployed state (E1) and the deployed state (E2). In contrast, the PRIOR ART stent 2, shown, for example in FIG. 13, has only two states, where the first stable state is the unexpanded or crimped state (S0) and the second stable state is the deployed state (S2).

Figure 5:
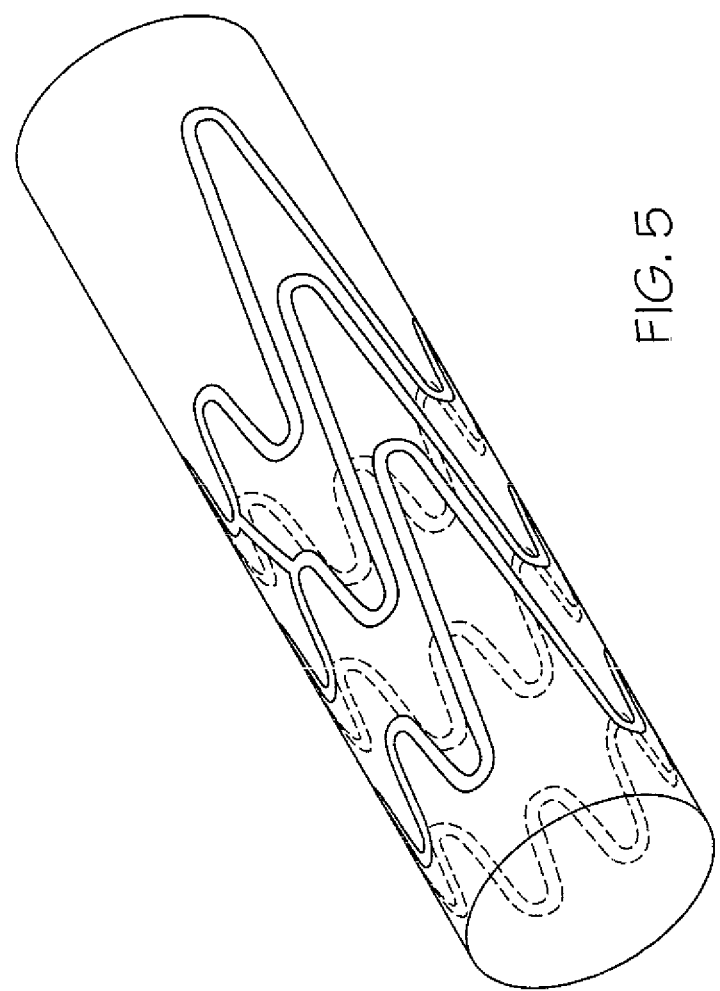
FIG. 5 is the stent pattern of FIG. 4 in a partially deployed state (E1).

As shown in FIG. 8, the stent 10 changes between the three states (E0,E1,E2) First, the stent 10 changes from the unexpanded state (E0) to the partially deployed state (E1). In some embodiments, the transition from the unexpanded state (E0) to the partially deployed state (E1) is caused by expansion of a balloon. In other embodiments, the stent 10 self-transitions from the unexpanded state (E0) to the partially deployed state (E1), which occurs, for example, if the first section 20 is made from shape memory material. In some embodiments, the first section 20 inverts when the stent 10 changes from the unexpanded state (E0) to the partially deployed state (E1), as shown, for example, in FIG. 8 The first section 20 can be described as inverting from a concave shape where the first section 20 is curved inwards, to a convex shape where the first section 20 is curved outwards In contrast to the first section 20, the second section 22 has the same shape, a convex shape in each stable state (E0,E1,E2) In other embodiments, the first section 20 only partially inverts when the stent 10 changes from the unexpanded state (E0) to the partially deployed state (E1), as shown, for example, in FIG. 5.

Figure 6:
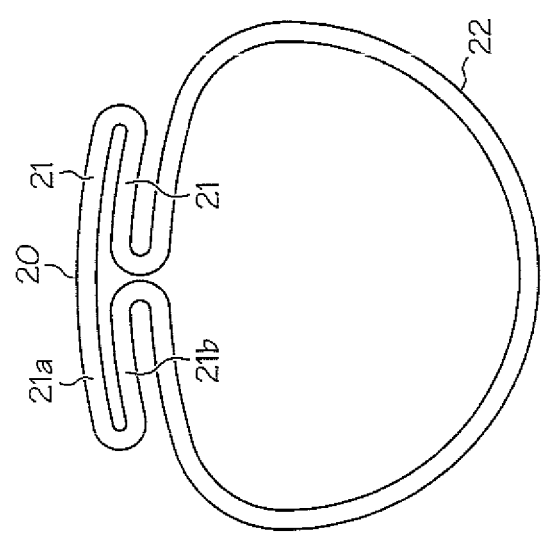
FIG. 6 is a cross-section of a stent in the unexpanded state with a first section that has overlapping portions.

In at least one embodiment, portions of the first section 20 slide away from one another when the stent 10 changes from the unexpanded state (E0) to the partially deployed state This occurs, for example, when the first section 20 has overlapping portions 21a,b, as shown in FIG. 6. In some embodiments, the overlapping portion 21a,b circumferentially slide apart as the stent 10 changes from the unexpanded state (E0) to the partially deployed state (E1) so that the overlapping portions 21a,b are circumferentially adjacent to one another instead of being overlapping.

Figure 14:
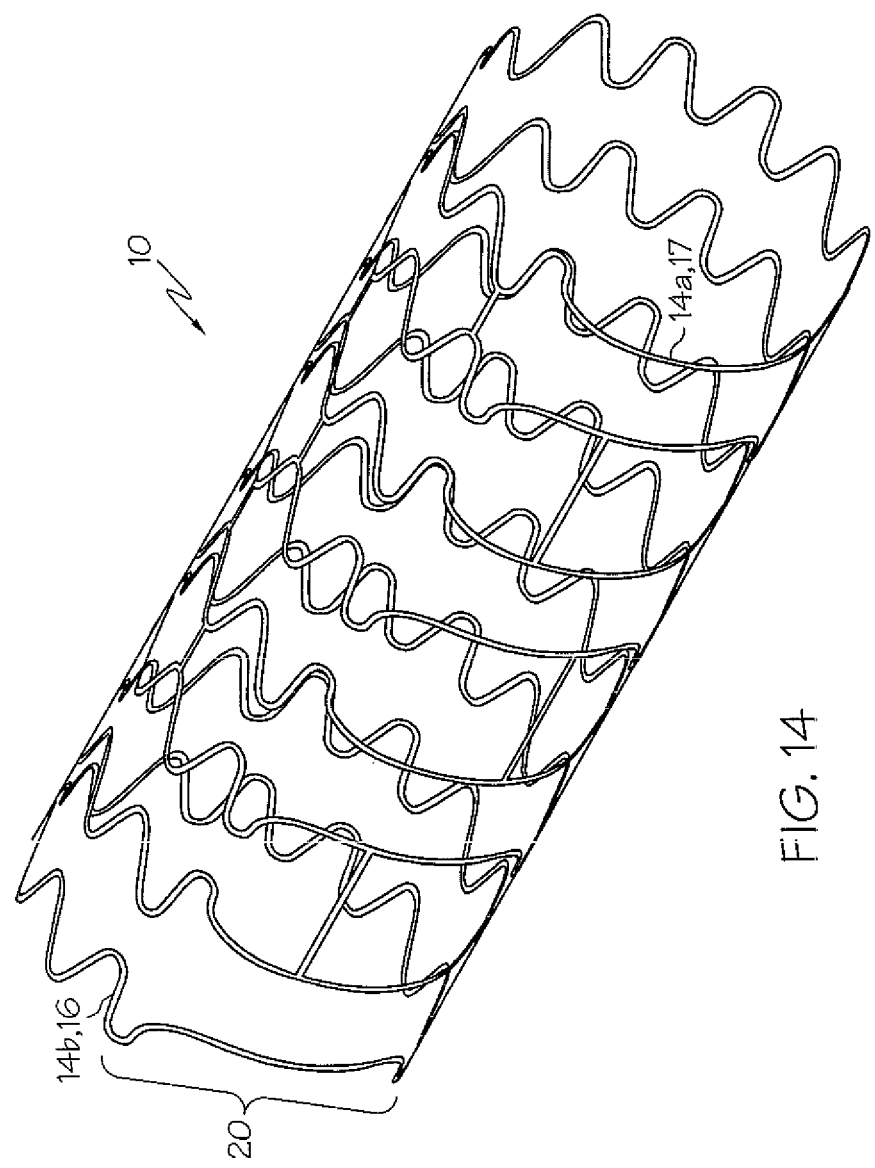
FIG. 14 is a perspective view of an inventive stent in a tubular state having the stent pattern of FIG. 1.

In some embodiments, the stent 10 snaps from the unexpanded state (E0) to the partially deployed state (E1). In this embodiment, the stent 10 is either in the unexpanded state (E0) or in the partially deployed state (E1). Thus the unexpanded state (E0) and the partially deployed state (E1) can be described as stable states As used in this application, a state is stable when the stent 10 remains in the state until acted upon by a force, for example heat or mechanical force. In one embodiment, the stent 10 snaps from the unexpanded state (E0) to the partially deployed state (E1) when the first members 14a are straight, as shown for example, in FIG. 14.

In other embodiments, the transition from the unexpanded state (E0) to the partially deployed state (E1) is continuous Thus, in this embodiment, the transition from the unexpanded state (E0) to the partially deployed state (E1) is not sudden. In one embodiment, this occurs when the first members 14a have a serpentine configuration In this embodiment, if the first section 20 is balloon expandable, the balloon transforms the stent 10 from a non-circular cross-sectional shape to a circular cross-sectional shape by the inversion of the first section 20 and then the balloon deforms the first members 14a in a manner similar to the deformation that occurs when a stent is deployed in a lumen.

In still other embodiments, the transition from the unexpanded state (E0) to the partially deployed state (E1) of the stent 10 occurs in both a sudden manner, i e in a snapping motion, and a continuous motion For example, if the first members 14a are slightly wavy, the first members 14a would first invert in a snap and then expand continuously as the slight wave of the first members 14a straightens.

The first section 20 can be described as having a first orientation or position relative to the longitudinal axis of the stent 10 in the first state (E0), and a second orientation or position relative to the longitudinal axis of the stent 10 in the second state (E1) where the first orientation is different than the second orientation For example, in FIG. 8, the first section 20 is oriented or positioned towards the longitudinal axis of the stent 10 in the first state (E0) and the first section 20 is oriented or positioned away from the longitudinal axis of the stent 10 in the second state (E1). In this embodiment, the first orientation is opposite the second orientation. In some embodiments, the first section 20 has the same shape in the first and second orientations. In other embodiments, the first section 20 has different shapes in the first and second orientations. For example, in FIG. 8, the first section 20 is U shaped in the first orientation and curvilinear in the second orientation.

Figure 13:
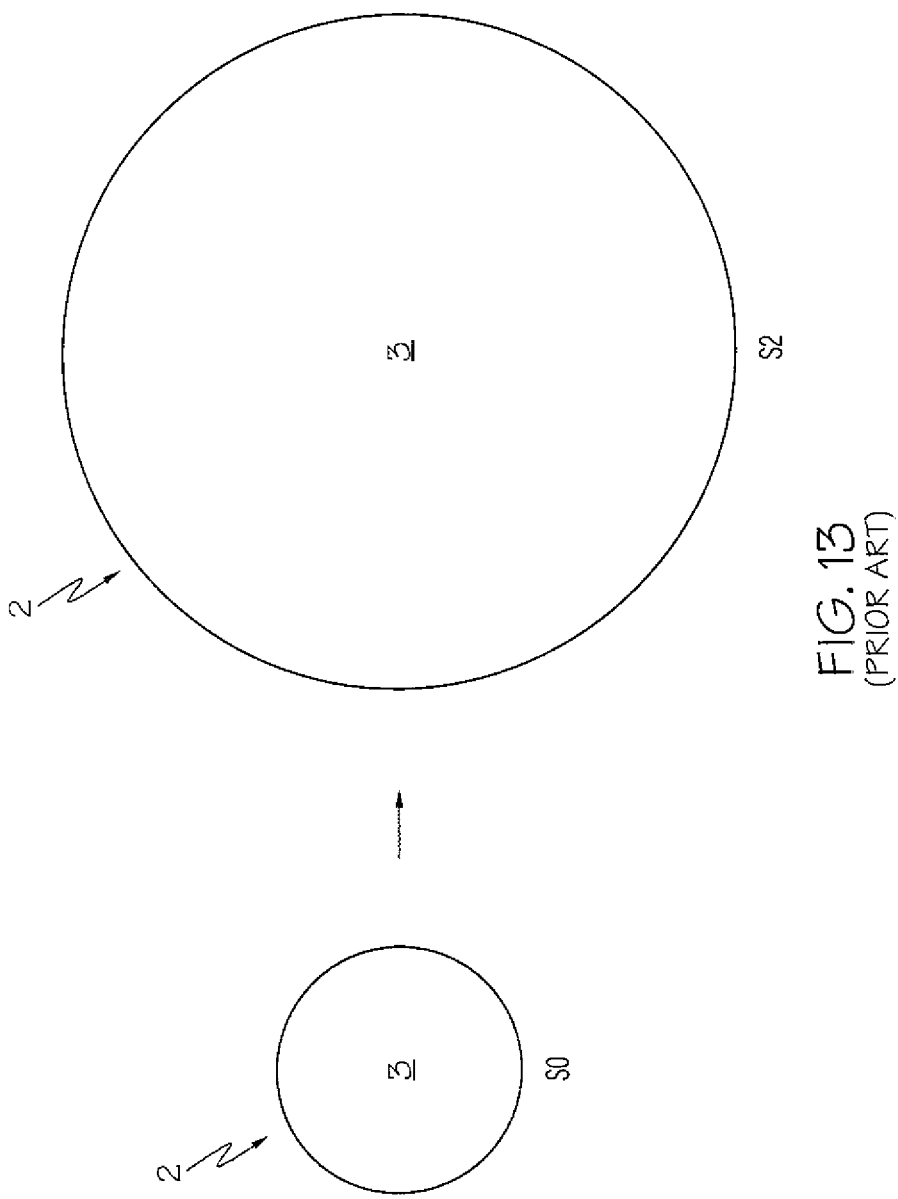
FIG. 13 is a cross-section of a PRIOR ART stent defining a lumen expanding from an unexpanded state to a deployed state.

After the stent 10 changes from the unexpanded state (E0) to the partially deployed state (E1), the stent 10 changes from the partially deployed state (E1) to the deployed state (E2), as shown, for example, in FIG 8. Thus, when the stent 10 is deployed in a body lumen, initially the stent 10 is in the unexpanded state (E0), then the stent changes to the partially deployed state (E1) and then the stent 10 changes to the deployed state (E2). In contrast, when the PRIOR ART stent 2 is deployed in a body lumen, the PRIOR ART stent 2 initially is in the unexpanded state (S0) then the PRIOR ART stent 2 changes to the deployed state (S2), as shown in FIG. 13. In some embodiments, the amount of plastic deformation required for the inventive stent 10 to change from the partially deployed state (E1) to the deployed state (E2) is less the amount of plastic deformation required for the PRIOR ART stent 2 to change from the unexpanded state (S0) to the deployed state (S2).

If the second section 22 of the stent 10 is made from balloon expandable material, balloon expansion of the stent 10 changes the state of the stent 10 from the partially deployed state (E1) to the deployed state (E2). In this embodiment, the balloon expandable stent 10 can be in a stable state that is between the partially deployed state (E1) and the deployed state (E2) depending upon the amount of stent expansion. Thus, the stent 10 in this embodiment has at least three stable states (E0,E1,E2) with a plurality of potential stable states between the partially deployed state (E1) and the deployed state (E2). If the second section 22 of the stent 10 is made from shape memory material, a stimulus such as heat, changes the state of the stent 10 from the partially deployed state (E1) to the deployed state (E2). In this embodiment, the stent 10 can be described as snapping from the partially deployed state (E1) to the deployed state (E2) and there are no stable states between the partially deployed state (E1) and the deployed state (E2). Thus, the stent 10 in this embodiment has only three stable states (E0,E1,E2).

Figure 21:
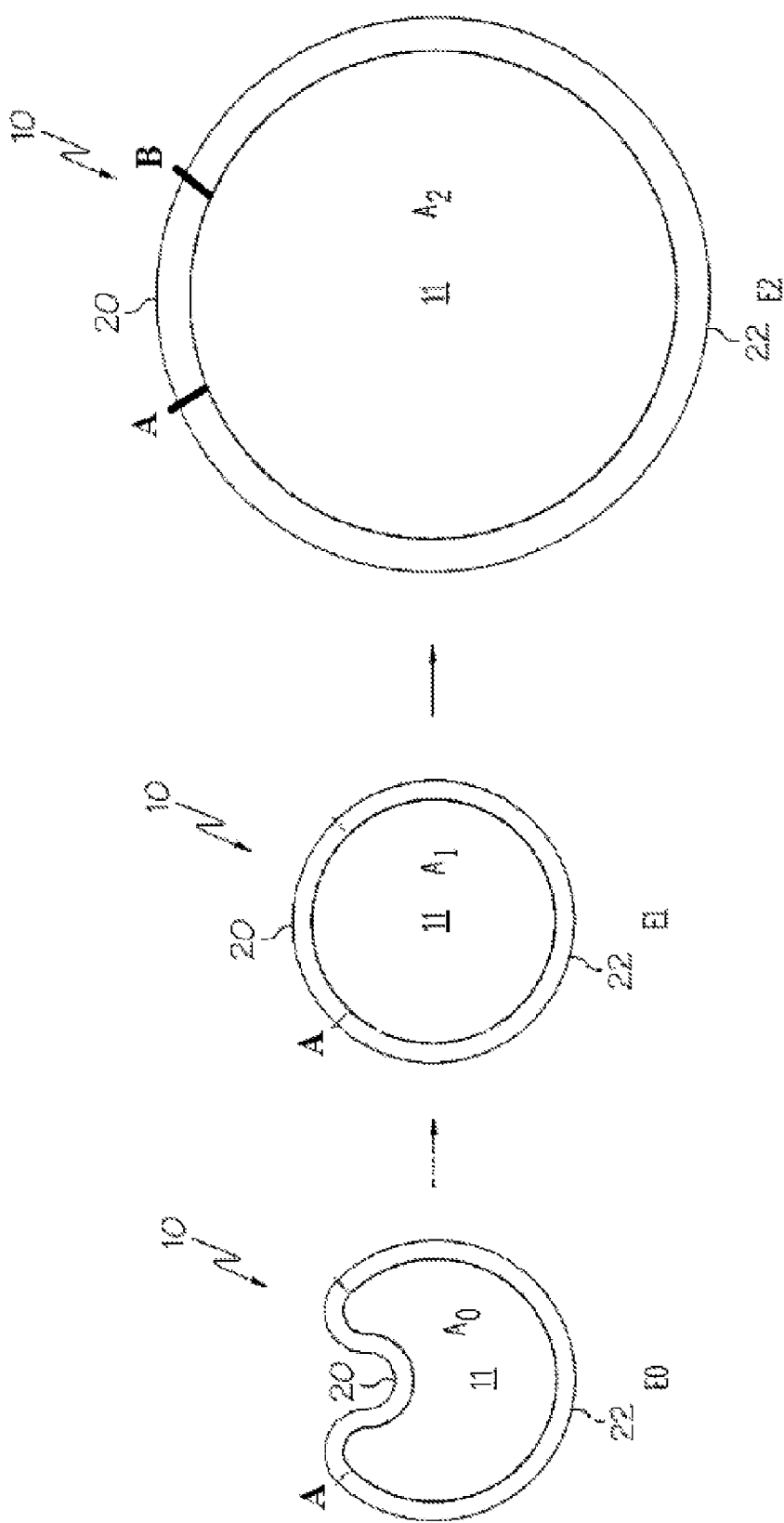
FIG. 21 is a schematic illustration of a stent in an unexpanded state, a partially deployed state, and a deployed state.

In at least one embodiment, the first section 20 does not expand when the stent 10 changes from the partially deployed state (E1) to the deployed state (E2) while the second section 22 expands when the stent 10 changes from the partially deployed state (E1) to the deployed state (E2). Thus, in this embodiment, the first section 20 has the same circumferential length in the unexpanded state (E0), the partially deployed state (E1), and the deployed state (E2), and the second section 22 has a first circumferential length in the unexpanded and partially deployed states (E0 and E1) and a second circumferential length in the expanded state (E2) where the second circumferential length is greater than the first circumferential length. This is shown schematically in FIG. 21.

In some embodiments, the total circumferential length of the stent 10 increases from the unexpanded state (E0) to the partially deployed state (E1) even though the circumferential length of the first section 20 does not change from the unexpanded state (E0) to the partially deployed state (E1) because at least a portion of the second section 22 flares out due to the inversion of first section 20. In one embodiment, the first and second ends of the first section 20 are positioned close together when the stent 10 is in the unexpanded state (E0) so that the first section 20 forms an almost fully closed circle. As shown in FIG. 6, for example, the first and second ends of the first section 20 do not form an almost fully closed circle because the first and second ends are positioned apart from one another.

In at least one embodiment, the ratio of the circumferential length of the first section 20 to the total circumferential length of the stent 10 is greater in the unexpanded state (E0) than in the deployed state (E2). In at least one embodiment, the ratio of the circumferential length of the first section 20 to the total circumferential length of the stent 10 in the unexpanded state (E0) is equal to the ratio of the circumferential length of the first section 20 to the total circumferential length of the stent 10 in the partially deployed state (E1). This is shown schematically in FIG. 21 where the first section has the same circumferential length in each state (E0, E1, and E2) and the second section has a greater circumferential length in the deployed state (E2) than in the unexpanded state (E0).

In at least one embodiment, the first section 20 and the second section 22 increase in circumferential length when the stent 10 changes from the partially deployed state (E1) to the deployed state (E2) In this embodiment, the first section 20 comprises first members 14a which are constructed and arranged to lengthen/increase in circumferential length when the stent 10 changes from the partially deployed state to the deployed state (E2). In some embodiments, the first members 14a are not straight so that the first members 14a can straighten and thereby increase in circumferential length when the stent 10 changes from the partially deployed state (E1) to the deployed state (E2). This can occur for example, when the first member 14a is curvilinear and therefore can straighten when the stent 10 changes to the deployed state (E2) (not shown) Note that the first member 14a does not need to be completely straight in the deployed state (E2), it can still be somewhat cuivrilinear in the deployed state (E2). In other embodiments, the first members 14a form a serpentine band, as shown, for example in FIG. 5, where the stent 10 is in the partially deployed state (E1). In this embodiment, when the stent 10 in FIG. 5 changes from the partially deployed state (E1) to the deployed state (E2), both the first members 14a and the second members 14b will increase in circumferential length as the serpentine configuration of the members 14a,b becomes straighter (not shown).

In at least one embodiment, the stent 10 has a first cross section and defines a lumen 11 that has a first cross-sectional shape in at least one of the states (E0, E1, or E2) and the stent 10 has a second cross-section and defines a lumen 11 that has a second cross-sectional shape in at least one other state (E0, E1 or E2), where the first cross-section is different from the second cross-section and the first cross-sectional shape is different from the second cross-sectional shape, as shown, for example, in FIG. 8 As used in this application, the cross-section of the stent 10 refers to the shape of the wall of the stent 10 formed by the plurality of members 14 defining the lumen 11 and the cross-sectional shape is the shape of the lumen 11 defined by the plurality of members 14 of the stent 10 in a cross-section.

In contrast, the PRIOR ART stent 2, has a circular cross-section and defines a lumen 3 that has a round shaped cross-sectional shape in both the first state, the unexpanded or crimped state (S0), and the second state, the deployed state (S2), as shown in FIG. 13 Thus, the PRIOR ART stent 2 has a first cross-section in both the unexpanded and deployed states (S0,S2) and the lumen 3 of the stent 2 has a first cross-sectional shape in both the unexpanded and deployed states (S0,S2).

In some embodiments, in the unexpanded state (E0), the stent 10 has a non-circular cross-section and defines a lumen 11 that has a non-round shaped cross-sectional shape; in the partially deployed state (E1), the stent 10 has a circular cross-section and defines a lumen 11 that has a round shaped cross-sectional shape; and in the deployed state (E2), the stent 10 has a circular cross-section and defines a lumen 11 that has a round shaped cross-sectional shape. This is shown, for example in FIG. 8 and FIGS. 9-11. In at least one embodiment, the stent 10 defines a lumen 11 having a first area ($A_1$) when the stent 10 is in the unexpanded state (E0) and a second area ($A_2$) when the stent 10 is in the partially deployed state (E1) and a third area ($A_3$) when the stent 10 is in the deployed state (E2), as shown in FIGS. 7-11. In some embodiments, the first area ($A_0$) is less than the second area ($A_0$, which is less than the third area ($A_2$).

In other embodiments, the stent 10 has a circular cross-section and defines a lumen 11 that has round shaped cross-sectional shape in the unexpanded state (E0), the partially deployed state (E1) and in the deployed state (E2) For example, the stent 10 embodiment shown in FIG. 6 has a substantially circular shaped cross-section in each state (E0, E1,E2).

Non-circular cross-sections include, but are not limited to, double C-shaped cross-section, double U-shaped cross-section, polygonal shaped cross-sections, irregular shaped cross-sections, symmetrical but not circular cross-sections, concave shaped cross-section, convex shaped cross-section, and any combination thereof Polygonal shaped, includes, for example, curved polygonal shaped, concave polygonal shaped, and convex polygonal shaped.

Figure 10:
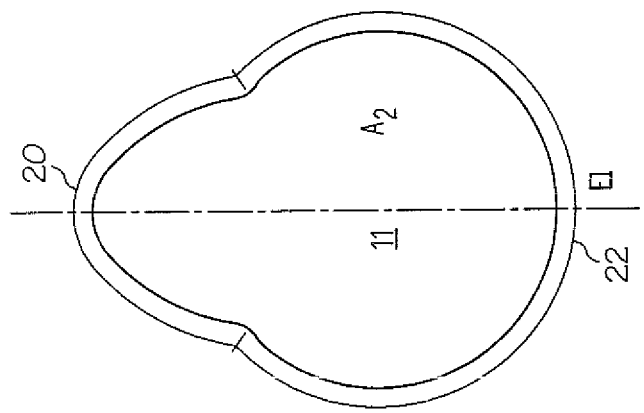
FIG. 10 is the stent of FIG. 9 in the second state, the partially deployed State.

In a double C-shaped or double U-shaped cross-section the stent 10 has two differently sized C shaped or U shaped sections 20,22 that are engaged to one another so that the smaller C or U shaped first section 20 is positioned at least partially within the larger sized C or U shaped second section 22. This is shown for example in FIGS. 7 and 9, which are two examples of a double C-shaped cross-section. The cross-section in FIG. 9 can also be described as a double U shaped cross-section or as a concave shaped cross-section. The cross-section of the stent 10 shown in FIG. 10, can be described as a symmetrical but not circular cross-section. The stent 10 cross-section in FIG. 10 is symmetrical because bisection of the stent 10 results in two mirror images, as shown by the dashed line bisecting the stent 10 Note that in these embodiments, at least a portion of the first section 20 can be described as having a shape that is complementary to the shape of at least a portion of the second section 22.

Figure 9:
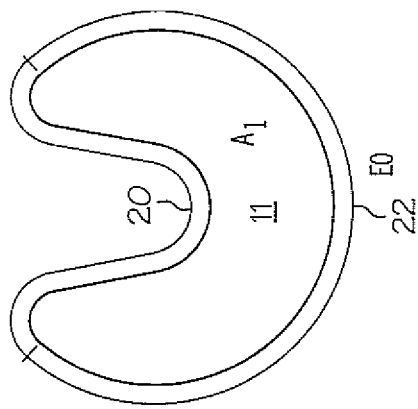
FIG. 9 is a cross-sectional view of another embodiment of the stent.

Examples of non-round shaped cross-sectional shapes include, but are not limited to, polygonal shaped, C-shaped, U-shaped, square shaped, irregular shaped, symmetrical but not circular shaped, concave shaped, convex shaped, and any combination thereof. A lumen 11 that has a C-shaped cross-sectional shape is shown, for example in FIG. 7 This cross-sectional shape can also be described as a concave shaped cross-section. A non-limiting example of a lumen 11 that has a U-shaped cross-sectional shape is shown in FIG. 9 A lumen 11 that has a symmetrical but not circular cross-sectional shape is shown, for example, in FIG. 10. The lumen 11 in FIG. 10 is symmetrical because bisection of the lumen 11 results in two mirror images, as shown by the dashed line bisecting the lumen 11.

As mentioned above, the stent 10 also has a pre-unexpanded state (pre-E0), not shown. In some embodiments, the stent 10 has a cross-sectional configuration in the pre-unexpanded state (pre-E0) that is different than the cross-sectional configuration in the unexpanded state (E0). In other embodiments, the stent 10 has the same cross-sectional configuration in both the pre-unexpanded state (pre-E0) and in the unexpanded state (E0).

Although the discussion above about the different states and cross-sectional shapes of the stent 10 focuses on the behavior of the sections 20,22 of the stent 10, since the sections 20,22 are formed of combination circumferential rings 19, as discussed below, the behavior of individual combination circumferential rings 19 is the same as described for the sections 20,22 of the stent 10. Thus, for example, each combination circumferential ring 19 transitions from the unexpanded state (E0) to the partially deployed state (E1) and then to the deployed state (E2) as described above and each circumferential ring 19 has a cross-section and defines a lumen having a cross-sectional shape as described above.

Figure 2:
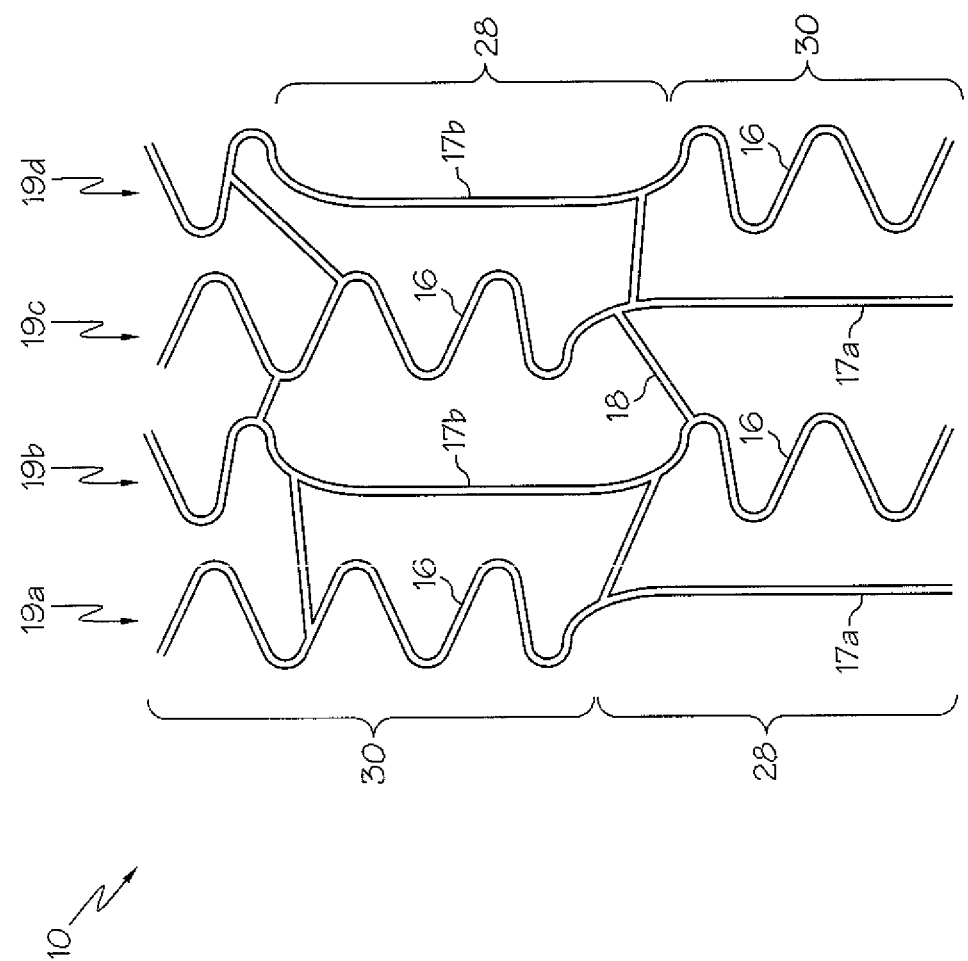
FIG. 2 is a flat view of a stent pattern comprising a plurality of circumferential bands where each circumferential band has a first portion and a second portion.
Figure 4:
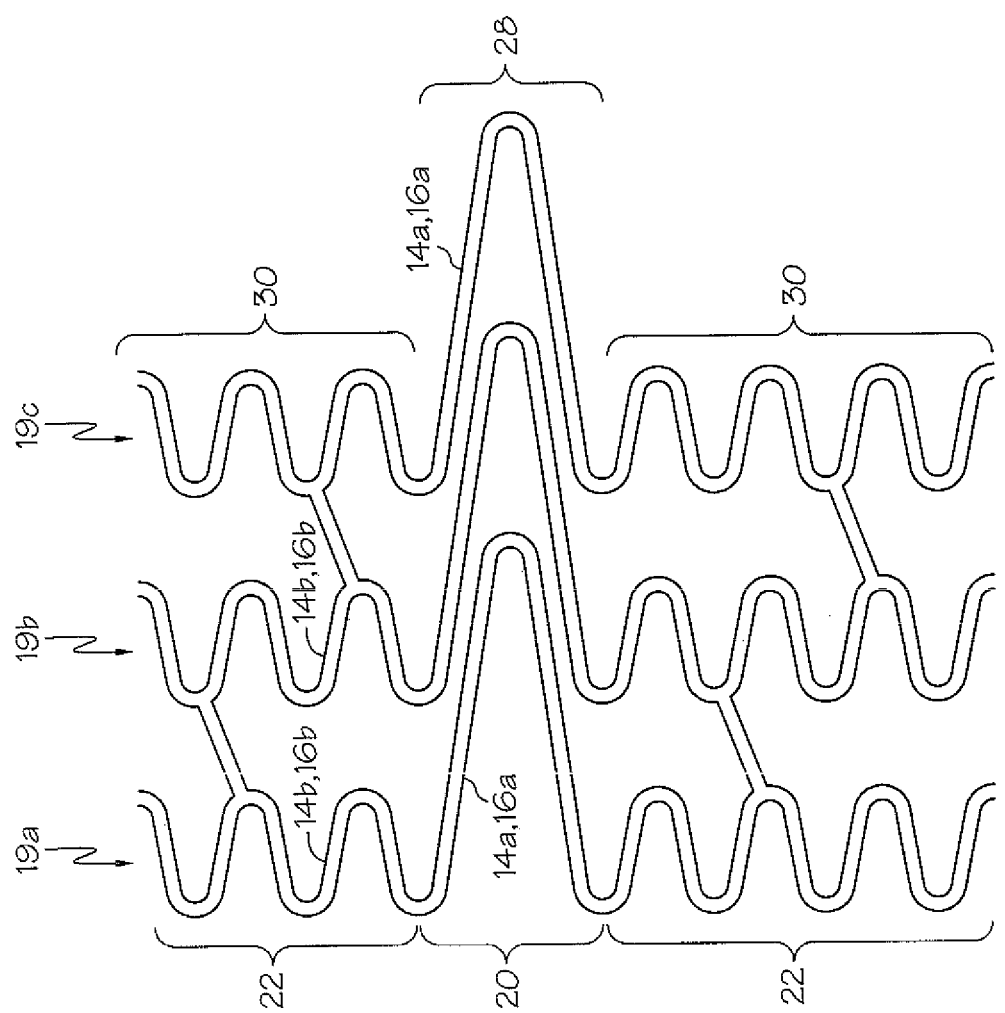
FIG. 4 is a flat view of a stent pattern that has two sections forming the circumference of the stent.

FIGS. 1, 2 and 4 are non-limiting examples of stent patterns for a stent 10 that has three stable states (E0,E1,E2) as discussed above. In at least one embodiment, the stent 10 comprises a plurality of circumferential rings 19 which are comprised of a plurality of members 14, as shown, for example, in FIG. 1. The stent 10 defines a plurality of cells 15 and defines a lumen 11. It is within the scope of the invention for the stent 10 to have one, two, three, four, five, six, seven, eight, nine, ten, or more circumferential rings 19. The plurality of members 14 includes struts 16, circumferential members 17, and connectors 18 As shown in FIG. 1, it is within the scope of the invention for each member 14 to have any configuration, for example, but not limited to, straight, curvilinear, zig-zag and any combination thereof. In at least one embodiment, each member 14 has the same thickness in a radial direction. As shown in FIG. 1, at least one connector 18 engages adjacent circumferential rings 19. It is within the scope of the invention for the connectors 18 to be peak to peak connectors 18a, peak to valley connectors 18b, valley to valley connectors (not shown), and/or any suitable connecting configuration.

In at least one embodiment, each circumferential ring 19 of the stent 10 has at least one first portion 28 and at least one second portion 30, as shown, for example, in FIGS, 1 and 2. Note that the configuration of the first portion 28 of the circumferential ring 19 affects the cross-section of the stent 10 and the cross-sectional shape of the lumen 11, as discussed above. As used in this application, a circumferential ring 19 that has at least one first portion 28 that has a configuration which gives the stent 10 a non-round shape cross-section in at least one of the three states (E0,E1,E2) is a combination circumferential ring 19 and a circumferential ring 19 that does not have any portions 28 which gives the stent 10 a non-round shape cross-section in any of the three states (E0, E1,E2) is a regular circumferential ring 19 In at least one embodiment, the stent 10 comprises at least one combination circumferential ring 19 and at least one regular circumferential ring 19 Examples of stents 10 that have at least one combination circumferential ring 19 and at least one regular circumferential ring 19 are discussed below.

It is within the scope of the invention for each circumferential ring 19 to have one, two, three, four, five, six or more first portions 28; one, two, three, four, five, six or more second portions 30; and any combination thereof. It is within the scope of the invention for the circumferential length of the first portion 28 to be about 25 percent to about 60 percent of the total circumferential length of the circumferential ring 19 when the stent 10 is in the unexpanded state. In some embodiments, the circumferential length of the first section 20 is at least 30% of the total circumferential length of the circumferential ring 19 when the stent 10 is in the unexpanded state. As discussed below in greater detail, the circumferential alignment of the first and second portions 28,30 of adjacent circumferential rings 19 form the first and second sections 20,22 of the stent 10.

It is within the scope of the invention for the stent 10 to be made from any material or combination of materials. It is also within the scope of the invention for the stent 10 to have any ductility or combination of ductilities. In at least one embodiment, the first portion(s) 28 of circumferential rings 19 is made from a first material and the second portion(s) 30 is made from a second material. In some embodiments, the first and second materials are the same. In other embodiments, the first material is different than the second material. In at least one embodiment, the first material has a first ductility and the second material has a second ductility In some embodiments the first and second ductilities are the same. In other embodiments, the first and second ductilities are different. As used in this application, a low ductile material has a ductility of no more than 15% and a ductile material has a ductility of at least 18%. In some embodiments, the first material is low ductile material and the second material is ductile material. In this embodiment, the circumferential ring 19 would have a first portion 28 that is a low-ductile portion and a second portion 30 that is a ductile portion. One of ordinary skill in the art will recognize that there are many different combinations of materials and ductilities for the portions of the stent 10 to have and all of these combinations are contemplated as being within the scope of the invention.

Non-limiting example of materials that can be used to make the stent 10 include, but are not limited to, biocompatible polymers, such as high density polyethylene (HDPE) and polyurethane, iron, iron alloys magnesium, magnesium alloys, zinc, zinc alloys, biodegradable polymers, and shape memory materials.

Examples of suitable iron alloys include iron-chromium-nickel alloys Some iron-chromium-nickel alloys are, eg by weight, 88-99.8% iron, 01-7% chromium, 0-3.5% nickel, and less than 5% of other elements (e g, magnesium and/or zinc), or 90-96% iron, 3-6% chromium and 0-3% nickel plus 0-5% other metals.

Examples of suitable magnesium alloys include magnesium-lithium-iron alloys; magnesium-aluminum-lithium-rare earth alloys; magnesium-lithium-aluminum-rare earth alloys; magnesium-aluminum-manganese-zinc alloys; magnesium-aluminum-manganese alloys; magnesium-lithium-other metals alloys; and magnesium-X-calcium alloys (e.g., Mg—Al—Si—Ca and Mg—Zn—Ca). Examples of rare earth metals that can be used include, but are not limited to, cerium, lanthanum, neodymium, praseodymium and any combination thereof.

Non-limiting examples of suitable alloys are, by weight, 50-98% magnesium, 0-40% lithium, 0-5% iron and less than 5% other metals or rare earths; 79-97% magnesium, 2-5% aluminum, 0-12% lithium and 1-4% rare earth; 85-91% magnesium, 6-12% lithium, 2% aluminum, 1% rare earth; 86-97% magnesium, 0-8% lithium, 2-4% aluminum and 1-2% rare earth; 89.2 to 90.9% magnesium, 8.5-9.5% aluminum, 0.15-0.4% manganese, 0.45-0.9% zinc; 55-65% magnesium, 30-40%) lithium and 0-5% other metals and/or rare earths. Other suitable alloys are described in U.S. Pat. No. 6,287,332 to Bolz entitled Implantable, Bioresorbable Vessel Wall Support, in Particular Coronary Stent, hereby incorporated by reference herein in its entirety.

Examples of suitable materials include biodegradable materials that are also biocompatible. By biodegradable is meant that a material will undergo breakdown or decomposition into harmless compounds as part of a normal biological process Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers Other polymers that may be used include polyester and polycarbonate copolymers. Examples of suitable metals include, but are not limited to, stainless steel, titanium, tantalum, platinum, tungsten, gold and alloys of any of the above-mentioned metals. Examples of suitable alloys include platinum-iridium alloys, cobalt-chromium alloys including Elgiloy and Phynox, MP35N alloy and nickel-titanium alloys, for example, Nitinol.

The stent 10 may be made of shape memory materials such as super elastic Nitinol or spring steel, or maybe made of materials which are plastically deformable. In the case of shape memory materials, the stent 10 may be provided with a memorized shape and then deformed to a reduced diameter shape. The stent 10 may restore itself to its memorized shape upon being heated to a transition temperature and having any restraints removed therefrom.

Other suitable materials for stent 10 include metallic materials, such as stainless steel (eg, 316 L, BioDur RTM 108 (UNS S29108), and 304 L stainless steel, and an alloy including stainless steel and 5-60% by weight of one or more radiopaque elements (e.g., Pt, Ir, Au, W) (PERSS RTM) as described in U.S. Application Publication No. 2003/0018380, U.S. Application Publication No. 2002/0144757, and U.S. Application Publication No. 2003/0077200, each of which are hereby incorporated by reference in their entirety, Nitinol (a nickel-titanium alloy), cobalt alloys such as Elgiloy, L.605 alloys, MP35N, titanium, titanium alloys (eg, Ti-6Al-4V, Ti-50Ta, Ti-10Ir), platinum, platinum alloys, niobium, niobium alloys (e g , Nb-1Zr) Co-28Cr-6Mo, tantalum, and tantalum alloys Other examples of materials are described in commonly assigned U.S. Application Publication No. 2005/0070990 and U.S. Application Publication No. 2006/0153729, each of which is hereby incorporated by reference in their entirety. Other materials include elastic biocompatible metal such as a superelastic or pseudo-elastic metal alloy, as described, for example, in commonly assigned U.S. Application Publication No. 2004/0143317, hereby incorporated by reference in its entirety.

It is within the scope of the invention for the members 14 of the circumferential ring 19 to form any pattern. In at least one embodiment, the members 14a forming the first portion 28 of the circumferential ring 19 form a different pattern 12 than the pattern 12 formed by the members 14b forming the second portion 30 of the circumferential ring 19. In some embodiments, the members 14a forming the first section 20 of the stent 10 are in the form of circumferential members 17 that extend circumferentially and the second members 14b forming the second section 22 of the stent 10 are in the form of struts 16 arranged in a serpentine ring, as shown, for example, in FIG. 1.

Figure 3:
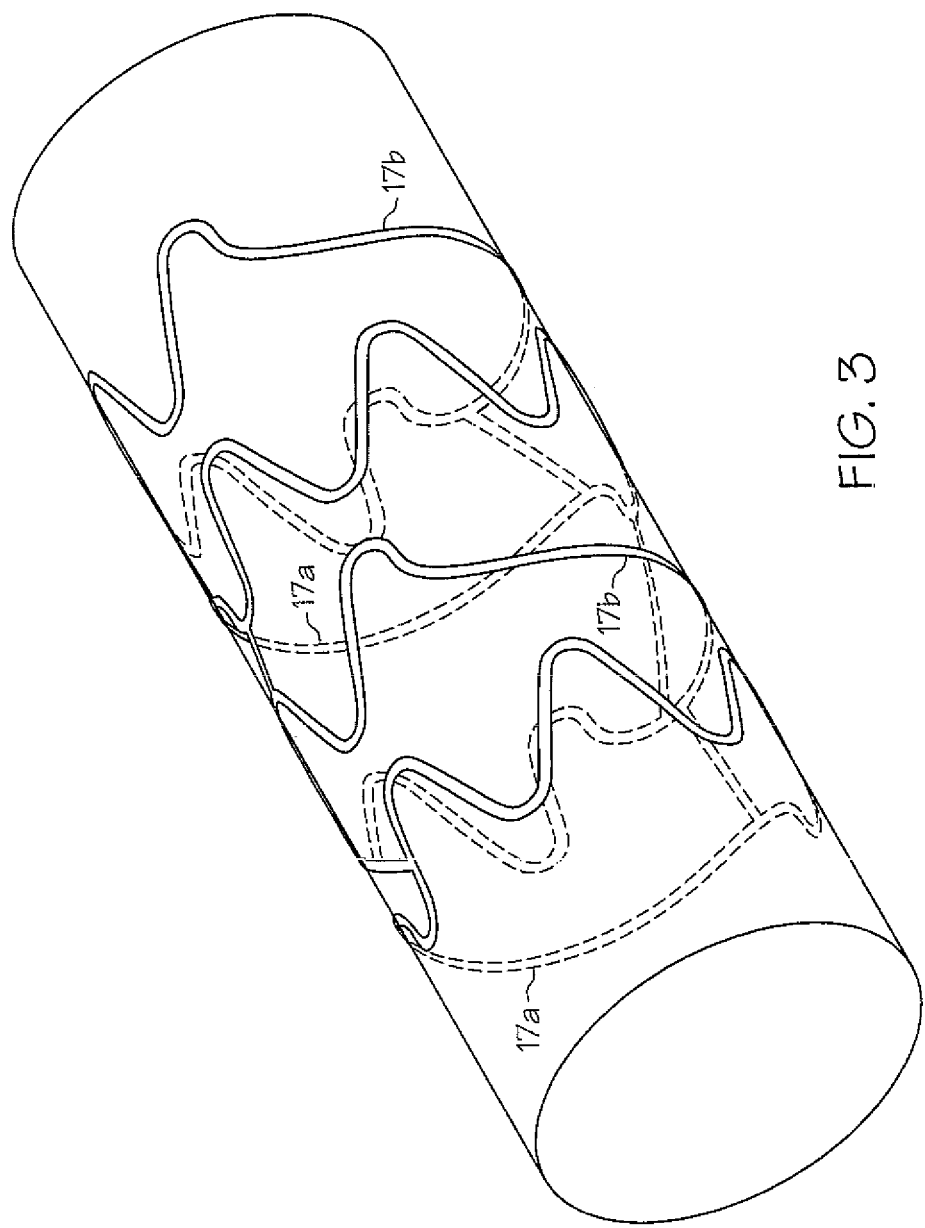
FIG. 3 is a schematic representation of the stent pattern of FIG. 2 in a tubular form.

In other embodiments, the first and second members 14a,b of the first and second portions 28,30 of the circumferential rings 19 are each arranged the same pattern, eg in a serpentine ring, as shown for example, in FIG. 3. Note that the longitudinal length or longitudinal extent of the first members 14a is greater than the longitudinal length or longitudinal extent of the second members 14b. Thus, the circumferential rings 19 can be described as comprising first members 14a with a first length and second members 14b with a second length, where the first length is greater than the second length.

As shown in FIG. 1, the circumferential members 17 of adjacent circumferential rings 19 are longitudinally separated from one another It is within the scope of the invention for adjacent circumferential members 17 to be longitudinally separated by any length. In at least one embodiment, the longitudinal length between two adjacent circumferential members 17 is at least equal to the length between two sides of a side branch ostium so that the stent 10 can be used at a bifurcation. Note that the circumferential members 17 can be described as connectors that engage the two edges 24,26 of the second section 22. In FIG. 1, each circumferential member 17 extends from a first edge 24 of the second section 22 to a second edge 26 of the second section 22, as represented by dashed lines. In this embodiment, the first edge 24 is parallel to the second edge 26 and both the first and second edges 24,26 of the second section 22 are parallel to the longitudinal axis of the stent 10, as shown in FIG. 1. In some embodiments, the first and second edges 24,26 are discontinuous, as shown in FIG. 1 In other embodiments, the first and second edges 24,26 are continuous.

As shown in FIG. 1, the circumferential members 17 are oriented at an angle to the longitudinal axis of the stent 10. In at least one embodiment, the circumferential members 17 are oriented from the first edge 24 of the second section 22 to the second edge 26 of the second section 22 at at least one angle relative to the longitudinal axis of the stent 10 Thus some of the circumferential members 17 can be oriented at a different angle than other of the circumferential members 17. In some embodiments, all of the circumferential members 17 are oriented at the same angle relative to the longitudinal axis of the stent 10. In at least one embodiment, at least some adjacent circumferential members 17 are engaged by a connector 18, as shown for example, in FIG. 1. In some embodiments, each adjacent pair of circumferential members 17 is engaged by a connector 18 In other embodiments, the circumferential members 17 are not engaged by a connector 18 As discussed above, the connector 18 can have any shape.

It is within the scope of the invention for the first portion(s) 28 of the circumferential rings 19 to have the same circumferential position about the circumference of the stent 10. This is shown, for example, in FIG. 1 where the circumferential members 17 of the first portions 28 have the same circumferential position along the longitudinal length of the stent 10. In at least one embodiment, the first portions 28 form a first section 20. A first section 20 is formed when the first portions 28 of at least two adjacent circumferential rings 19 of the stent 10 have the same circumferential position This is shown, for example, in FIGS. 1 and 14 where the first portions 28 of adjacent circumferential rings 19 form a first section 20 that extends along the longitudinal length of the stent 10, a longitudinal first section 20. Additionally it is within the scope of the invention for the first section 20 to have the same circumferential length along the longitudinal length of the first section 20, as shown, for example, in FIG. 1. Similarly, a second section 22 is formed when the second portions 30 of at least two adjacent circumferential rings 19 of the stent 10 have the same circumferential position.

In at least one embodiment, the first section 20 does not extend along the entire longitudinal length of the stent 10. In some embodiments, the longitudinal length of the first section 20 is at least 25 percent (25%) of the longitudinal length of the stent 10. In other embodiments, the longitudinal length of the first section 20 is about twenty five percent (25%) to about seventy-five percent (75%) of the longitudinal length of the stent 10. In at least one embodiment, the stent 10 has a proximal portion comprising combination circumferential rings 19 and a distal portion comprising regular circumferential rings 19. In some embodiments, the stent 10 having this configuration has a stepped configuration in the expanded state (E2) for example, the proximal portion of the stent 10 has a larger diameter than the distal portion when the stent 10 is in the expanded state (E2).

Figure 12:
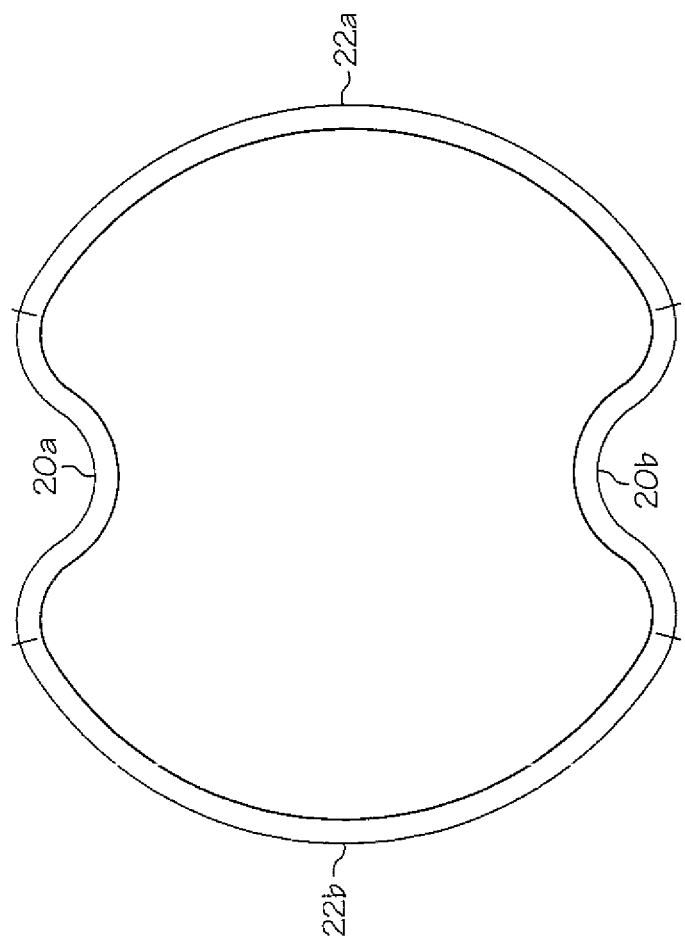
FIG. 12 is a cross-sectional view of another embodiment of the stent.

In some embodiments, each circumferential ring 19 of the stent 10 is a combination circumferential ring 19. Therefore, it is within the scope of the invention for the stent 10 to have two, three, four, five, six, seven, eight, nine, ten, or more, first and second sections 20,22 about the circumference of the stent 10. The stent 10 in FIG. 1 has one first section 20 and one second section 22 about the circumference of the stent 10. As shown in FIG. 12, the stent 10 has two first sections 20a,b and two second sections 22a,b about the circumference of the stent 10 and/or along the longitudinal length of the stent 10. In some embodiments, each first section 20a is positioned opposite from another first section 20b and each second section 22a,b is positioned opposite from another second section 22a,b when the stent 10 is in the tubular form, as shown, for example, in FIG. 12. In other embodiments, the first sections 20 are positioned opposite second sections 22.

Figure 7:
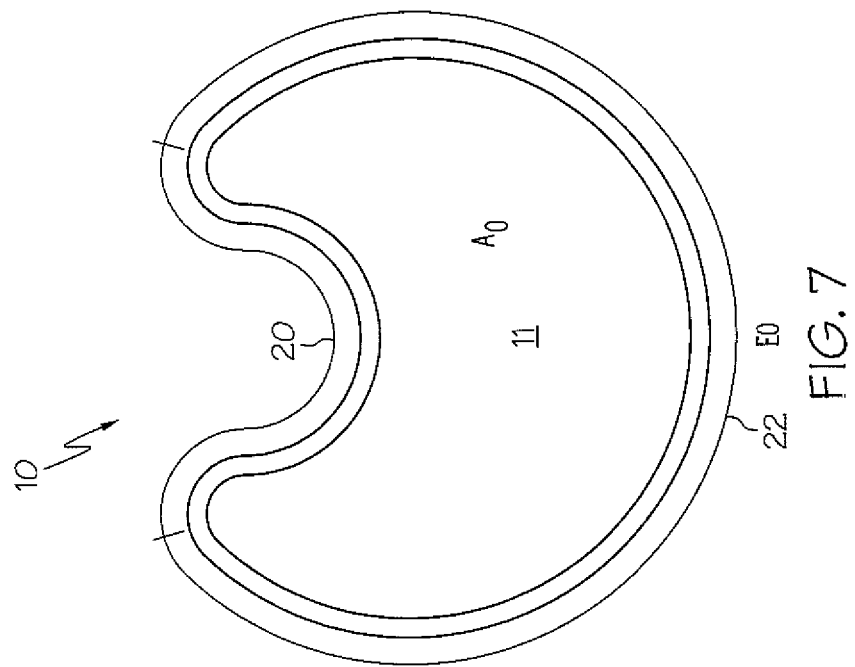
FIG. 7 is a cross-sectional view of an embodiment of the stent.

Since the first section(s) 20 and the second seetion(s) 22 form the circumference of the stent 10, each section 20,22 has a circumferential length less than the total circumferential length of the stent 10, as shown, for example, in FIG. 7. As used in this application, the total circumferential length is the length about the entire circumferential perimeter of the stent 10. Thus, the total circumferential length would be the sum of the length of the first section 20 and the length of the second section 22 It is within the scope of the invention for the circumferential length of the first section 20 to be about 25 percent (25%) to about 60 percent (60%) of the total circumferential length when the stent 10 is in the unexpanded state. In some embodiments, the circumferential length of the first section 20 is at least thirty percent (30%) of the total circumferential length.

In at least one embodiment, the circumferential length of the first section 20 varies along the longitudinal length of the stent 10 while the circumferential position of the first section 20 is the same along the longitudinal length of the stent 10. In this embodiment, the circumferential position of the first section 20 can be determined by a line that is parallel to the longitudinal axis of the stent 10 and that bisects the first section 20 in half. In one embodiment, the stent 10 comprises a first portion and a second portion where the circumferential length of the first section 20 in the first portion is greater than in the second portion and the circumferential position of the first section 20 is the same in the first and second portions. In this embodiment, the first portion of the stent 10 has a greater diameter than the second portion of the stent 10 when the stent 10 is in the deployed state (E2). Thus, the stent 10 would have a stepped configuration in the deployed state (E2).

In another embodiment, the circumferential length of the first section 20 gradually increases along the longitudinal length of the stent 10 and the circumferential position of the first section 20 is the same along the longitudinal length of the stent 10 In one embodiment, the circumferential length of the first section 20 gradually increases from about twenty-five percent (25%) of the total circumferential length to about sixty percent (60%) of the total circumferential length In this embodiment, the stent 10 has a tapered diameter in the deployed state (E2), with the stent 10 having a smaller diameter when the first section 20 comprises about twenty-five percent (25%) of the total circumferential length and a larger diameter when the first section 20 comprises about sixty percent (60%) of the total circumferential length. Thus, the diameter increases and the circumferential length of the first section 20 increases.

It is also within the scope of the invention for the first portions 28 of the combination circumferential rings 19 to have different circumferential positions along the longitudinal length of the stent 10 This is shown, for example, in FIG. 2 where the circumferential member 17 forming the first portion 28 of one circumferential ring 19 has a different circumferential position than the circumferential member 17 of an adjacent circumferential ring 19, FIG. 3 shows the flat stent pattern of FIG. 2 in tubular form. As shown in FIG. 2, the circumferential members 17a of the first and third combination circumferential rings 19a,c have the same circumferential position and the circumferential members 17b of the second and fourth combination circumferential rings 19b,d have the same circumferential position that is different from the circumferential position of the circumferential members 17 of the first and third combination circumferential rings 19a,c. One of ordinary skill in the art will recognize that there are many different combinations of circumferential positions for the first portions 28 of the combination circumferential rings 19 to have.

In some embodiments, the first portions 28 of adjacent combination circumferential rings 19 form a first section 20 that extends in a helix along the longitudinal length of the stent 10, a helical first section 20. Thus, the circumferential positions of the first portions 28 of adjacent combination circumferential rings 19 each have a slightly different circumferential position along the longitudinal length of the stent 10 In this embodiment, the first and second edges 24,26 of the second section 22 are at an angle to the longitudinal axis of the stent 10.

In at least one embodiment, the invention is directed towards a method of making the inventive stent 10. In at least one embodiment, the inventive stent 10 is made by cutting a stent pattern into a stent tube 8 where the stent tube 8 has a non-circular cross-section and that defines a lumen that has a non-round shaped cross-sectional shape In some embodiments, the diameter of the stent tube 8 is substantially the same along the longitudinal length of the stent tube 8. In other embodiments, the stent tube 8 has at least two diameters. In one embodiment, a stent tube 8 with a first section having a first diameter and a second section having a second diameter, larger than the first diameter, is used to form a stent 10 with a stepped configuration In another embodiment, the stent tube 8 has a tapered diameter. In this embodiment, a tapered stent 8 is formed In some embodiments, the stent tube 8 is made from at least one low-ductile material and at least one ductile material. As discussed above, the stent 10 can be made from any material or combination of materials, therefore, it is within the scope of the invention for the stent tube 8 to be made from two, three, four, five, six, seven, eight, or more different materials Additionally, as discussed above, it is within the scope of the invention for the stent tube 8 to have one, two, three, four, five, six, seven, eight, or more ductilities. This type of stent tube 8 can be used to make a stent 10 with a plurality of ductilites.

In some embodiments, a laser that has a dynamic Z-adjustment for the focusing lens is used to cut the stent pattern into the stent tube 8. The dynamic Z-adjustment is used to control the depth at which the laser beam is focused Examples of non-circular cross-sections and non-round shaped cross-sectional shapes are discussed in greater detail above.

Another method of making the inventive stent 10 comprises obtaining a first stent tube 8a and a second stent tube 8b where the first stent tube 8a has a diameter that is smaller than the diameter of the second stent tube 8b. In at least one embodiment, both the first and second tubes 8a,b have a substantially round shape cross-section In some embodiments, the first tube 8a has a first cross-section and the second tube 8b has a second cross-section that is different than the first cross-section One non-limiting example is when the first tube 8a has an oval shaped cross-section and the second tube 8b has a round shaped cross-section. In some embodiments, the first stent tube 8a is made from low ductile material and the second stent tube 8b is made from ductile material.

A portion of the first tube 8a is laser cut with the pattern for the first section 20 and a portion of the second tube 8b is laser cut with the pattern for the second section 22. Then the first section 20 and the second section 22 of the tubes 8a,b are cut out and the excess portion of the tubes 8a,b are removed Then the first and second sections 20,22 are joined together to form the stent 10. It is within the scope of the invention for the first and second sections 20,22 to be joined in any suitable manner, for example, but not limited to being laser welded.

In some embodiments, the first and second sections 20,22 are joined together so that the stent 10 is ready to be crimped onto a balloon catheter, i.e. the stent 10 is in the unexpanded state (E0), shown, for example in FIG.20a. In other embodiments, the first and second sections 20,22 are joined together so that the stent 10 requires further processing before it is ready to be crimped onto a balloon catheter, i.e. the stent 10 is in the pre-unexpanded state (pre-E0), shown for example in FIG. 20b. An example of further processing is a pre-crimping step, as discussed in greater detail below.

In at least one embodiment, if the stent 10 is made from Nitinol, the stent 10 can be made by cutting a stent pattern into a Nitinol stent tube to form the stent 10, then heat-setting the stent 10 when it is in the deployed configuration (E2), and then subsequently deforming the stent 10 to the unexpanded state configuration (E0) as it is being inserted into a suitable delivery catheter As discussed above, the Nitinol stent tube can have one or more diameters along the length of the stent tube.

In at least one embodiment, if the inventive stent 10 is made from a polymer, the stent 10 can be made by injection molding the polymer into the desired shape Any other suitable technique which is known in the art or which is subsequently developed may also be used to manufacture the inventive stent 10.

Figure 15:
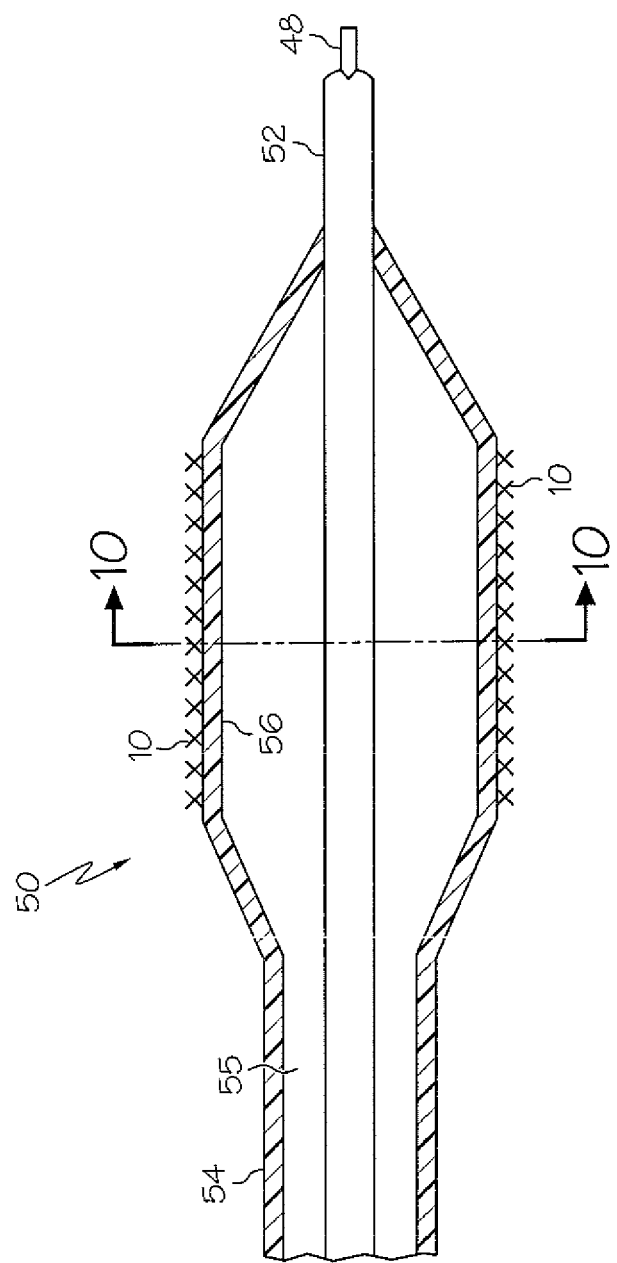
FIG. 15 is a side view of a partial longitudinal cross section of a balloon catheter with the inventive stent crimped onto the balloon.

In at least one embodiment, the invention is directed towards crimping the stent 10 onto a balloon catheter 50 In at least one embodiment, the invention is directed towards a catheter assembly comprising a balloon catheter 50 and the stent 10. As shown by the partial longitudinal cross-section in FIG. 15, the balloon catheter 50 comprises a balloon 56, an inner shaft 52, an outer shaft 54 and a guidewiie 48. The outer shaft 54 defines an inflation lumen 55 and the inner shaft 52 defines a guide wire lumen 53 As is known in the art, a first end of the balloon 56 is engaged to the outer shaft 54 of the balloon catheter 50 and a second end of the balloon 56 is engaged to the inner shaft 52 of the balloon catheter 50. In at least one embodiment, the balloon 56 has at least one fold or wing 58. In some embodiments, the balloon 56 has two folds 58. In other embodiments, the balloon 56 has one T-fold 58. The at least one fold or wing 58 can be made by any method. It is within the scope of the invention for the at least one fold/wing 58 of the balloon 56 to be made by any method.

Figure 16:
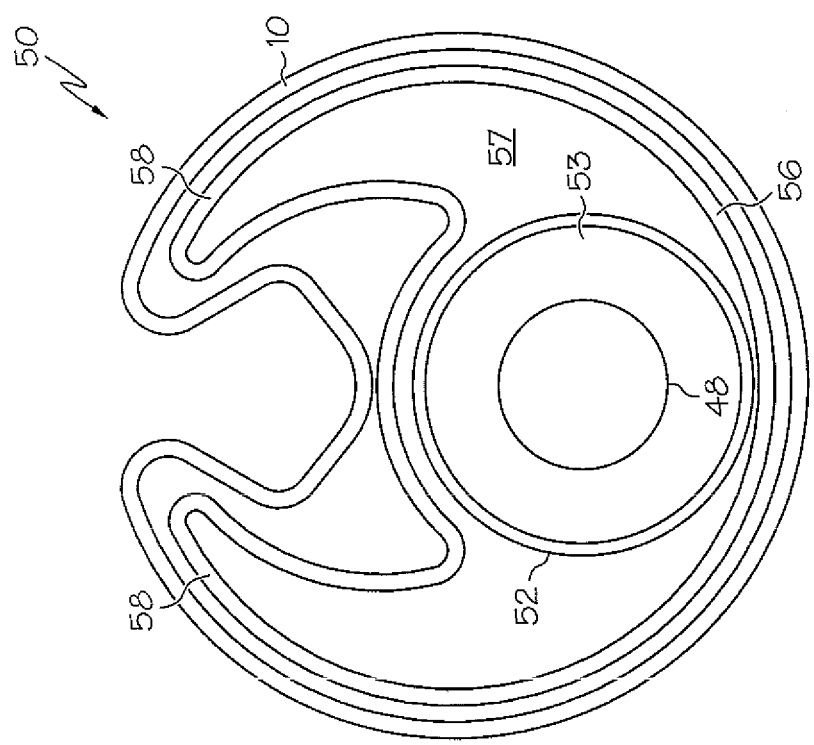
FIG. 16 is a cross-section of an embodiment of the balloon catheter of FIG. 15.

In at least one embodiment, the inner shaft 52 of the balloon catheter 50 has a circular cross-section, as shown, for example, in FIG. 16 In this embodiment, the inner shaft 52 defines a guide wire lumen 53 that has a round-shaped cross-sectional shape. In some embodiments, the entire longitudinal length of the inner shaft 52 has a circular cross-section and defines a guide wire lumen 53 that has a round-shaped cross-sectional shape. In at least one embodiment, the inner shaft 52 of the balloon catheter 50 has a non-circular cross-section, as shown, for example, in FIG. 17. In this embodiment, the inner shaft 52 defines a guide wire lumen 53 that has a non-round shaped cross-sectional shape In some embodiments the longitudinal length of the inner shaft 52 has a proximal section and a distal section where the proximal section the inner shaft 52 has a circular cross-section and defines a guide wire lumen 53 that has a round-shaped cross-sectional shape and the distal section of the inner shaft 52 has a non-circular cross-section and defines a guide wire lumen 53 that has a non-round shaped cross-sectional shape.

In at least one embodiment, the stent 10 is crimped onto the balloon 56 of a balloon catheter 50. In some embodiments, the crimping procedure involves a pre-crimping step and a crimping step In at least one embodiment, the stent 10 changes from the pre-unexpanded state (pre-E0) to the unexpanded state (E0) during the crimping step In one embodiment, the pre-crimping step modifies the cross-section of at least a portion of the stent 10 For example, a stent 10 that has a round shaped cross-section is modified to have a non-round shaped cross-section, which for example could be the cross-section desired for the stent 10 in the unexpanded state (E0).

In other embodiments, the crimping procedure does not have a pre-crimping step This occurs, for example, if the stent 10 is in the unexpanded state (E0) before it is to be crimped onto the balloon catheter 50. For example, a stent 10 made from a stent tube 8 having the desired cross-section as described above is in the unexpanded state (E0) and can be crimped onto the balloon catheter 50 without a pre-crimping step.

Figure 17:
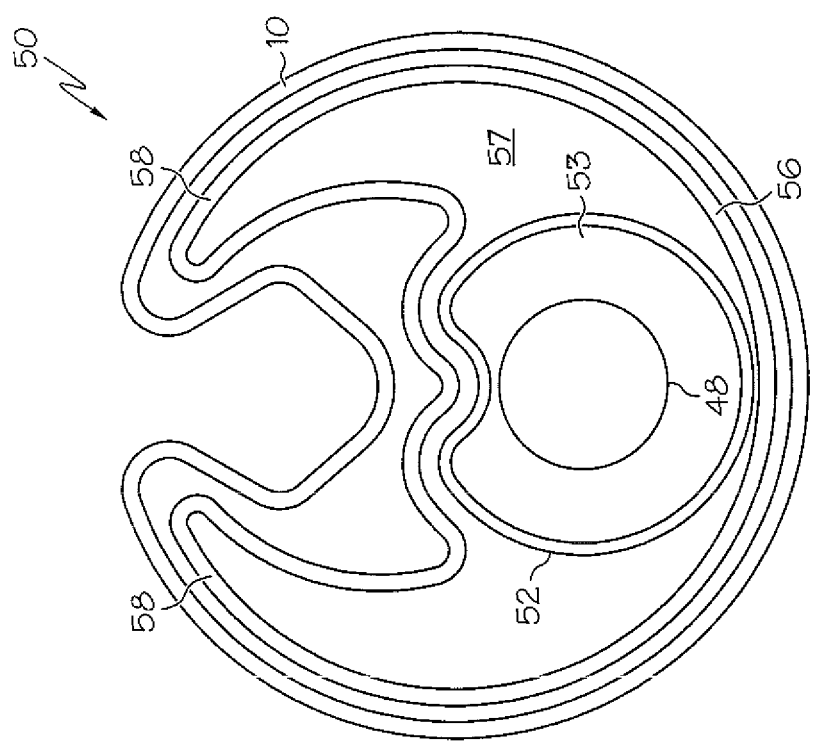
FIG. 17 is a cross-section of another embodiment of the balloon catheter of FIG. 15.

In one embodiment, the pre-crimping step comprises disposing the stent 10 about the balloon 56 of the balloon catheter 50 so that the first section(s) 20 of the stent 10 is aligned with the at least one fold 58 of the balloon 56. Then the first section(s) 20 is pushed inwards towards the inner shaft 52 so that the first section(s) 20 is positioned in between the folds 58 of the balloon 56, as shown in FIGS 16-17. In at least one embodiment, at least one rod is used to push the first section(s) 20 of the stent 10 inwards towards the inner shaft 52 of the balloon catheter 50. At this point the stent 10 is ready to be crimped onto a balloon catheter 50. In at least one embodiment, the rod has a configuration that is complementary to the configuration of the first section 20 being pushed inwards by the rod Thus, for example, if the first section 20 is a longitudinal first section 20, then the rod is substantially straight, or if the first section 20 is a helical first section 20, then the rod has a helical configuration. In at least one embodiment, the rod has a length at least equal to the length of the first section 20. In some embodiments, the rod is a metal pin In at least one embodiment, the at least one rod is engaged to an inside surface of a tube, as discussed below in greater detail.

After the pre-crimping step where the first section(s) 20 of the stent 10 has been positioned between the folds 58 of the balloon 50, the stent 10 is crimped onto the balloon 56 In some embodiments, the rod/metal pin is removed before the stent 10 is crimped onto the balloon 56. It is within the scope of the invention for the stent 10 to be crimped onto the balloon 56 in any manner In this method of crimping, the wrapping of the balloon 56 is done only after the balloon 56 is placed in the stent 10 and the stent 10 is wrapped together with the balloon 56.

Figure 18:
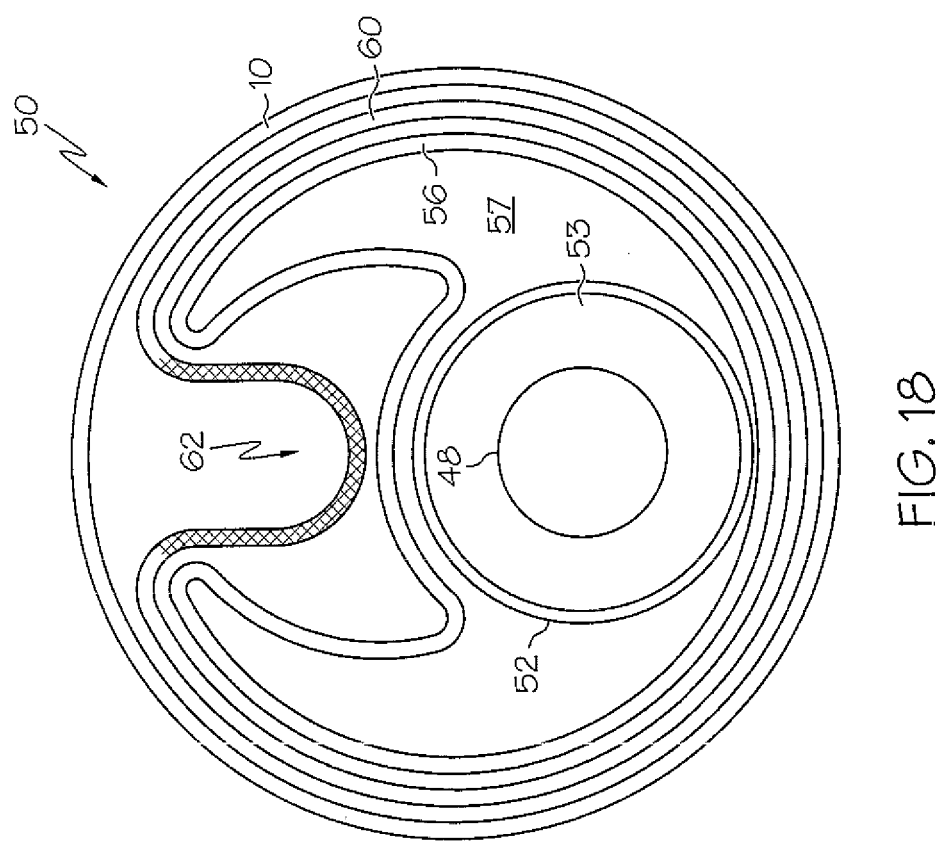
FIG. 18 is a cross-section of a stent disposed about a balloon catheter with a tube positioned between the stent and the balloon

In another embodiment, the pre-crimping step comprises disposing the stent 10 about the balloon 56 of a balloon catheter 50 and positioning a tube 60 between the stent 10 and the balloon 56. An example of this assembly 10/56/60 is shown, for example, in FIG. 18. It is within the scope of the invention for the tube 60 to be made of any material, for example, but not limited to metals, or plastics such as silicone. In some embodiments, the tube 60 has a non-round shaped cross-section Thus, the tube 60 has at least one shaping region 62, indicated in FIG. 18 by cross-hatching. In some embodiments, the cross-section of the tube 60 is substantially the same as the cross-section of the stent 10 when the stent 10 is in the unexpanded state (E0). Non-limiting examples of cross-sections that a stent 10 can have are discussed above.

In at least one embodiment, the tube 60 has at least one rod engaged to the interior surface of the tube 60 (not shown) In this embodiment, the at least one rod can be described as a shaping region 62. It is within the scope of the invention for the rod to be made from any material and for the rod to be engaged to the interior surface of the tube 60 by any suitable means In some embodiments, the tube 60 is a casted polymer structure that has thicker portions In at least one embodiment, the tube 60 with the at least one rod has a round shaped cross-section. In one embodiment, the tube 60 with at least one rod is used in the pre-crimping step of a stent 10 that has first sections 20 at variable circumferential positions, as shown, for example, in FIG. 2. In another embodiment, the tube 60 has one to and is used in the pre-crimping step of a stent 10 with at least one first section 20, e.g a horizontal first section 20 or a helical first section 20.

Figure 19:
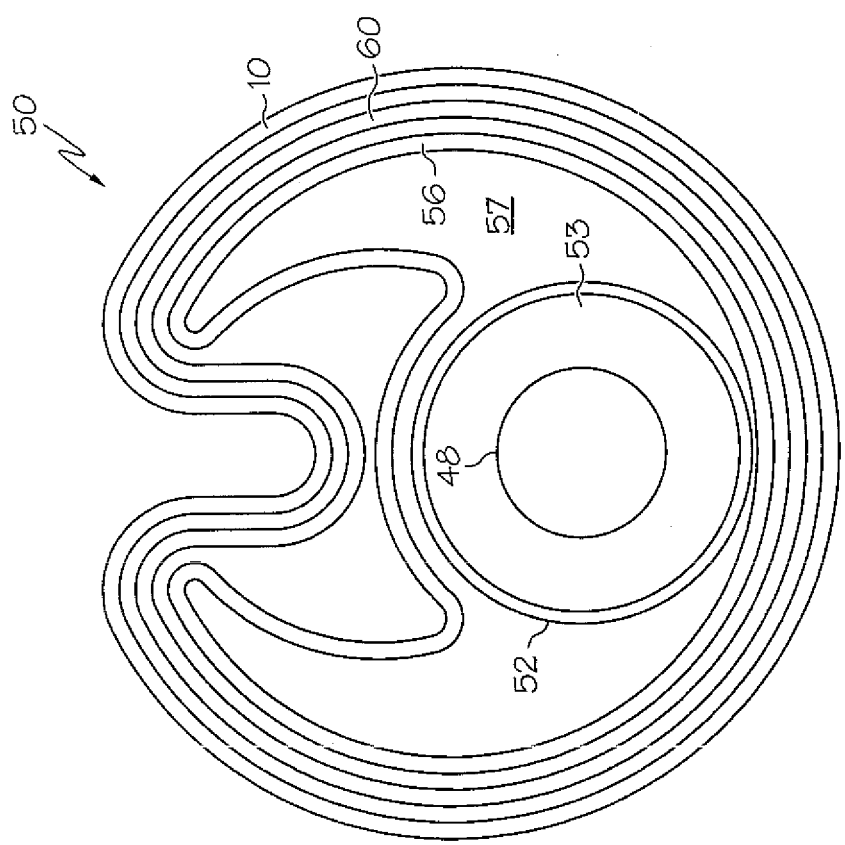
FIG. 19 is the cross-section of FIG. 18 after the stent has been deformed

In at least one embodiment, during the pre-crimping step, pressure is applied to the assembly 10/56/60 so that the first section(s)/first position(s) 20,28 assume their unexpanded configuration. In some embodiments, hydrostatic compression is used. Thus, the stent 10 and the tube 60 are aligned so that the first section(s)/first portion(s) 20,28 of the stent 10 is disposed over the shaping region(s) 62 of the tube 60. A cross-section of the assembly 10/56/60 of FIG. 18 after pressure has been applied is shown in FIG. 19 After the tube 60 is removed from between the stent 10 and the balloon 56, the stent 10 can be crimped onto the balloon 56. In at least one embodiment, the tube 60 has a lubricant on the inner and outer surfaces so that the tube 60 can be easily removed from between the stent 10 and the balloon 56.

In the stent 10 embodiment where the first section(s) 20 has overlapping portions 21, the pre-crimping step comprises crimping the first section(s) 20 so that the first section(s) 20 has overlapping portions 21, as shown, for example in FIG, 6. After the overlapping portions 21 are made in the first section(s) 20, the stent 10 is crimped onto the balloon catheter 50. An example of a crimper that can be used to form the overlapping portions 21 of the first section(s) 20 is described in greater detail in commonly assigned Patent Application Publication No 2007/0123970, entitled Bifurcation Stent With Overlapping Crimped Struts, hereby incorporated by reference in its entirety.

In at least one embodiment, the stent 10 is crimped onto the balloon catheter 50 by a crimper comprising at least one first crimping member and at least two second crimping members. An example of a suitable crimper is described in greater detail in commonly assigned Patent Application Publication No. 2007-0123970. In this embodiment, the at least one first crimping member crimps the first section(s) 20 towards the inner shaft 52 and then the second crimping members crimp the stent 10 onto the balloon catheter 50. Thus the number of first crimping members is equal to the number of first sections 20. Note that the crimper can be used for both the pre-crimping step and the crimping step.

In some embodiments the stent 10, the delivery system or other portion of the assembly may include one or more areas, bands, coatings, members, etc that is (are) detectable by imaging modalities such as X-Ray, MRI, ultrasound, etc. In some embodiments at least a portion of the stent 10 and/or adjacent assembly is at least partially radiopaque.

In some embodiments the at least a portion of the stent 10 is configured to include one or more mechanisms for the delivery of a therapeutic agent Often the agent will be in the form of a coating or other layer (or layers) of material placed on a surface region of the stent 10, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

At least one of the inventions discussed above can be described by the following numbered statements:

1. A stent, the stent an unexpanded state and a partially deployed state, the stent having a circumference and comprising a first section and a second section, the first and second sections forming the circumference of the stent;
  the first section having a first shape in both the unexpanded state and the partially deployed state; and
  the second section having a first shape in the unexpanded state and a second shape different than die first shape in the partially deployed state.

2. The stent of statement 1, the first section comprising a plurality of members having a ductility of at least 18%, and the second section comprising a plurality of members having a ductility of no more than 15%.

3. The stent of statement 1, the ductility of the plurality of members of the first section being between about 18 percent to about 20 percent.

4. The stent of statement 1, the ductility of the plurality of members of the second section being between about 10 percent to about 15 percent.

5. The stent of statement 1, the stent having a total circumferential length about a longitudinal axis of the stent, the first section having a first circumferential length, the second section having a second circumferential length, the total circumferential length of the stent being equal to the sum of the first and second circumferential lengths, the second circumferential length being less than the first circumferential length.

6 The stent of statement 5, the stent having a longitudinal length, wherein the second section extends along the entire longitudinal length of the stent.

7. The stent of statement 1, the stent having a non-circular cross-sectional geometry in an unexpanded state.

8. The stent of statement 7, the non-circular cross-sectional geometry being C shaped or U-shaped.

9. The stent of statement 1, the stent further having a deployed state, the stent having a circular cross-sectional geometry in the deployed state.

10. The stent of statement 1, the plurality of members forming the second section being made from at least one member of the group consisting of magnesium alloys, iron alloys, and any combination thereof.

11. A method of crimping a stent onto a balloon catheter, the balloon catheter comprising a balloon, the method comprising
  disposing a stent about the balloon of the balloon catheter, the stent having at least one first section, the balloon having at least two folds, the stent being disposed about the balloon so that the at least one first section is aligned with the at least two folds of the balloon;
  pushing the first section towards the balloon so that the first section is positioned between the at least two folds of the balloon; and
  crimping the stent onto the balloon.

12. The method of statement 11, the balloon catheter further comprising an inner shaft and an outer shaft, the outer shaft being disposed about a portion of a length of the inner shaft, a first end of the balloon being engaged to the outer shaft and a second end of the balloon being engaged to the inner shaft, the inner shaft defining a guide wire lumen, the guide wire lumen having a shape, the shape of the guide wire lumen being selected from at least one member of the group consisting of a substantially round shape, a non-round shape and any combination thereof.

13. The method of statement 12, the non-round shape being selected from at least one member of the group consisting of U-shaped, C-shaped, polygonal shaped, symmetrical but not round shaped, and any combination thereof.

14. The method of statement 11, a rod being used for pushing the first section towards the balloon.

15. A method of manufacturing a stent from a stent tube, comprising cutting a first stent pattern and a second stent pattern into the stent tube, the stent tube defining a lumen that has a cross-section that is non-round shaped.

16. A stent, the stent comprising a plurality of combination circumferential rings, each of the plurality of combination circumferential rings comprising at least one first strut and at least one second strut, the at least one first strut having a ductility of at least 18% and the at least one second strut having a ductility of no more than 15%.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent, the stent comprising a plurality of members and having a circumference, the plurality of members defining a lumen, the stent having three states, the three states being an unexpanded state, a partially deployed state, and a deployed state, the lumen having a first cross-sectional shape in the unexpanded state, a second cross-sectional shape in the partially deployed state and a third cross-sectional shape in the deployed state, the first cross-sectional shape of the lumen being different from the second and third cross-sectional shapes of the lumen, the first cross-sectional shape of the lumen being a non-round shaped cross-sectional shape, the unexpanded state being a stable state wherein the first cross-sectional shape is maintained without requiring a restraint to maintain the first cross-sectional shape.

2. The stent of claim 1, the first cross-sectional shape of the lumen being selected from at least one member of the group consisting of U-shaped, C-shaped, polygonal shaped, symmetrical but not round shaped, irregular shaped, concave shaped, and any combination thereof.

3. The stent of claim 1, the second and third cross-sectional shapes of the lumen being the same cross-sectional shape.

4. The stent of claim 3, the second and third cross-sectional shapes of the lumen being a substantially round-shaped cross-sectional shape.

5. The stent of claim 1, the second cross-sectional shape of the lumen being different than the third cross-sectional shape of the lumen, the second cross-sectional shape of the lumen being a non-round shaped cross-sectional shape.

6. The stent of claim 5, the second cross-sectional shape of the lumen being selected from at least one member of the group consisting of polygonal shaped, symmetrical but not round shaped, irregular shaped, convex shaped, and any combination thereof.

7. The stent of claim 1, the plurality of members comprising
a first group of members, the first group of members forming a first section, the first group of members having a ductility of no more than 15%; and
a second group of members, the second group of members forming a second section, the second group of members having a ductility of at least 18%;
wherein the first and second section forming at least a portion of the circumference of the stent.

8. The stent of claim 7, the first group of members being made from a magnesium alloy.

9. The stent of claim 7, the first group of members forming a first pattern, the second group of members forming a second pattern, the first pattern different from the second pattern.

10. The stent of claim 9, the first pattern comprising a plurality of circumferential members longitudinally separated from one another, the second pattern comprising a plurality of struts and a plurality of connectors, the plurality of struts forming a plurality of circumferential rings, adjacent circumferential rings being engaged by a portion of the plurality of connectors.

11. The stent of claim 7, the first and second sections forming the circumference of the stent,
the first section having a first circumferential length when the stent is in the unexpanded state, a second circumferential length when the stent is in the partially deployed state, and a third circumferential length when the stent is in the deployed state, the first, second and third circumferential lengths being the same length;
the second section having a first circumferential length when the stent is in the unexpanded state, a second circumferential length when the stent is in the partially deployed state and a third circumferential length when the stent is in the deployed state, the third circumferential length being greater than the first and second circumferential lengths.

12. The stent of claim 7, the first and second sections forming the circumference of the stent, the stent having a first circumference in the unexpanded state, a second circumference in the partially deployed state and a third circumference in the deployed state, the first section having a first circumferential length in the unexpanded state, a second circumferential length in the partially deployed state and a third circumferential length in the deployed state, the ratio of first circumferential length to first circumference being greater than the ratio of the third circumferential length to the third circumference.

13. The stent of claim 7, the first section having a first shape in the unexpanded state and a second shape in the partially deployed state, the second shape being the inverse of the first shape.

14. The stent of claim 7, the first section having a first shape in the unexpanded state, a second shape in the partially deployed state, and a third shape in the deployed state, the first shape being different from the second and third shapes of the stent, and the second shape being the same as the third shape.

15. The stent of claim 14, the first shape being selected from at least one member of the group consisting of U-shaped, C-shaped, polygonal shaped, irregular shaped, symmetrical but not circular shaped, concave shaped, and any combination thereof.

16. The stent of claim 14, the second section having the same shape in the unexpanded state, the partially deployed state, and the deployed state.

17. The stent of claim 14, at least a portion of the first shape of the first section being complementary to at least a portion of the shape of the second section in the unexpanded state.

18. The stent of claim 7, the first and second sections forming the circumference of the stent, the stent having a first cross-section in the unexpanded state, the first cross section being selected from at least one member of the group consisting of double U-shaped, double C-shaped, polygonal shaped, symmetrical but not circular shaped, irregular shaped, concave shaped, and any combination thereof.

19. A stent, the stent comprising a plurality of members and having a circumference, the plurality of members defining a lumen, the stent having three states, the three states being an unexpanded state, a partially deployed state, and a deployed state, the lumen having a first cross-sectional shape in the unexpanded state, a second cross-sectional shape in the partially deployed state and a third cross-sectional shape in the deployed state, the first cross-sectional shape of the lumen being different from the second and third cross-sectional shapes of the lumen, the first cross-sectional shape of the lumen being selected from at least one member of the group consisting of U-shaped, C-shaped, polygonal shaped, symmetrical but not round shaped, irregular shaped, concave shaped, and any combination thereof, wherein the first cross-sectional shape of the lumen is maintained without restraining the plurality of members.

20. A stent, the stent having a circumference, the stent comprising
a first group of members, the first group of members forming a first section, the first group of members having a ductility of no more than 15%;
a second group of members, the second group of members forming a second section, the second group of members having a ductility of at least 18%;
the first and second sections forming at least a portion of the circumference of the stent, the stent having three states, the three states being an unexpanded state, a partially deployed state, and a deployed state;
the first section having concave shape in the unexpanded state, a convex shape in the partially deployed state and a convex shape in the deployed state, wherein the concave shape is maintained without restraining the first group of members; and
the second section having a convex shape in each state.

* * * * *